United States Patent [19]
Farrell et al.

[11] Patent Number: 6,075,008
[45] Date of Patent: Jun. 13, 2000

[54] METHOD FOR PROMOTING CELL PROLIFERATION AND GROWTH

[75] Inventors: Catherine L. Farrell, Agoura; Francis H. Martin, Newbury Park, both of Calif.; Rachel Yabkowitz, Whitehouse Station, N.J.

[73] Assignee: Amgen Inc., Thousand Oaks, Calif.

[21] Appl. No.: 09/190,889

[22] Filed: Nov. 12, 1998

Related U.S. Application Data

[62] Division of application No. 08/735,041, Oct. 22, 1996, Pat. No. 5,914,251.

[51] Int. Cl.[7] .......................... A61K 38/18; C07K 14/475
[52] U.S. Cl. ................................. 514/12; 514/2; 530/399
[58] Field of Search ................................ 530/399; 514/2, 514/12

[56] References Cited

FOREIGN PATENT DOCUMENTS

| | | |
|---|---|---|
| 0 690 127 | 3/1996 | European Pat. Off. . |
| WO 96/04379 | 2/1996 | WIPO . |
| WO 96/17933 | 6/1996 | WIPO . |

OTHER PUBLICATIONS

Hillier et al., "zc48f02.r1 Soares senescent fibroblasts NbHSF Homo sapiens cDNA clone 325563 5'", EMBL Sequence Database, XP–002052756, Jun. 3, 1996.

Hillier et al., "zw46a12.r1 Soares total fetus NB2HF8 9w Homo sapiens cDNA clone 773086 5'" similar to TR:G12303965 Bone Derived Growth Factor, May 24, 1997.

Boring et al., CA Cancer J. Clin., vol. 44, No. 1, pp. 7–26 (1994).
Scher, Curr. Opinion Oncol., vol. 3, pp. 568–574 (1991).
Franks, J. Pathology and Bacteriology, vol. 73, pp. 603–611 (1956).
Huben et al., CA Cancer J. Clin., vol. 36, No. 5, pp. 274–292 (1986).
Zetter et al., Prostate Cancer and Bone Metastasis, Ed. by Karr and Yamanaka, Plenum Press, NY (1992), pp. 39–43.
Jacobs, Urology, vol. 21, No. 4, pp. 337–344 (1983).
Logothetis et al., Seminars in Oncology, vol. 21, No. 5, pp. 620–629 (1994).
Thompson, Cancer Cells, vol. 2, No. 1, pp. 345–354 (1990).
Scher et al., Seminars in Urology, vol. 10, No. 11, pp. 55–64 (1992).
Chackal–Roy et al., J. Clin. Invest., vol. 84, pp. 43–50 (1992).
Chung, Cancer Biol., vol. 4, pp. 183–192 (19930.
Gleave et al., Cancer Res., vol. 51, pp. 3753–3761 (1991).
Chakal Rossi et al., Proc. Natl. Acad. Sci. USA, vol. 89, pp. 6197–6201 (1992).
Lewin, Science, vol. 237, p. 1570 (1987).
Reeck et al., Cell, vol. 50, p. 667 (1987).
George et al., Macromolecular Sequencing and Synthesis, pp. 127–149 (1988).

*Primary Examiner*—John Ulm
*Assistant Examiner*—Christine Saoud
*Attorney, Agent, or Firm*—Richard J. Mazza; Ron K. Levy; Steven M. Odre

[57] ABSTRACT

A method is disclosed which provides for the proliferation and growth of cells, such as prostate cells, by contacting them with an effective amount of a placental-derived prostate growth factor.

5 Claims, 13 Drawing Sheets

FIG. 1A

| | | | | | | | | | | | | | | | | |
|---|---|---|---|---|---|---|---|---|---|---|---|---|---|---|---|---|
| ATG | GAA | TCC | AGG | TCC | TTC | TAT | ACC | GCT | TAC | CTG | CAG | AGA | CTC | TCT | GGG | 48 |
| Met | Glu | Ser | Arg | Ser | Phe | Tyr | Thr | Ala | Tyr | Leu | Gln | Arg | Leu | Ser | Gly | |
| 1 | | | | 5 | | | | | 10 | | | | | 15 | | |
| CTC | ACC | AGG | GAG | GCT | GCC | CAG | ACC | ACA | GTT | GCA | CCA | ACC | ACT | GCT | AAC | 96 |
| Leu | Thr | Arg | Glu | Ala | Ala | Gln | Thr | Thr | Val | Ala | Pro | Thr | Thr | Ala | Asn | |
| | | | 20 | | | | | 25 | | | | | 30 | | | |
| AAG | ATA | GCT | CCC | ACT | GTT | TGG | AAA | TTG | GCA | GAT | CGC | TCC | AAG | ATC | TAC | 144 |
| Lys | Ile | Ala | Pro | Thr | Val | Trp | Lys | Leu | Ala | Asp | Arg | Ser | Lys | Ile | Tyr | |
| | | 35 | | | | | 40 | | | | | 45 | | | | |
| ATG | GCT | GAC | CTG | GAA | TCT | GCA | CTG | CAC | TAC | ATC | CTG | CGG | ATA | GAA | GTG | 192 |
| Met | Ala | Asp | Leu | Glu | Ser | Ala | Leu | His | Tyr | Ile | Leu | Arg | Ile | Glu | Val | |
| | 50 | | | | | 55 | | | | | 60 | | | | | |
| GGC | AGG | TTC | CCG | GTC | CTG | GAA | GGG | CAG | CGC | CTG | GGT | GGC | CCT | GAA | AAA | 240 |
| Gly | Arg | Phe | Pro | Val | Leu | Glu | Gly | Gln | Arg | Leu | Gly | Gly | Pro | Glu | Lys | |
| 65 | | | | | 70 | | | | | 75 | | | | | 80 | |
| GTT | TGT | GGC | AGT | TCT | GGC | CAA | GTA | TTT | CCT | GGG | CGG | CCC | TTA | GTC | CAG | 288 |
| Val | Cys | Gly | Ser | Ser | Gly | Gln | Val | Phe | Pro | Gly | Arg | Pro | Leu | Val | Gln | |
| | | | | 85 | | | | | 90 | | | | | 95 | | |
| AAC | TTT | CTG | CAC | TCC | GTG | AAT | GAA | TGG | CTC | AAG | AGG | CAG | AAG | AGA | AAT | 336 |
| Asn | Phe | Leu | His | Ser | Val | Asn | Glu | Trp | Leu | Lys | Arg | Gln | Lys | Arg | Asn | |
| | | | 100 | | | | | 105 | | | | | 110 | | | |
| AAA | ATT | CCC | TAC | AGT | TTC | TTT | AAA | ACT | GCC | CTG | GAC | GAC | AGG | AAA | GAG | 384 |
| Lys | Ile | Pro | Tyr | Ser | Phe | Phe | Lys | Thr | Ala | Leu | Asp | Asp | Arg | Lys | Glu | |
| | | | 115 | | | | 120 | | | | | 125 | | | | |
| GGT | GCC | GTT | CTT | GCC | AAG | AAG | GTG | AAC | TGG | ATT | GGC | TGC | CAG | GGG | AGT | 432 |
| Gly | Ala | Val | Leu | Ala | Lys | Lys | Val | Asn | Trp | Ile | Gly | Cys | Gln | Gly | Ser | |
| | 130 | | | | | 135 | | | | | 140 | | | | | |
| GAG | CCG | CAT | TTC | CGG | GGC | TTT | CCC | TGC | TCC | TGT | GGG | TCC | TCT | TCC | ACT | 480 |
| Glu | Pro | His | Phe | Arg | Gly | Phe | Pro | Cys | Ser | Cys | Gly | Ser | Ser | Ser | Thr | |
| 145 | | | | | 150 | | | | | 155 | | | | | 160 | |
| TCT | AGA | CTG | TGC | AGG | CAG | CTC | GGA | TCA | AAA | TGT | AGA | CCA | CTC | ACA | GGA | 528 |
| Ser | Arg | Leu | Cys | Arg | Gln | Leu | Gly | Ser | Lys | Cys | Arg | Pro | Leu | Thr | Gly | |
| | | | | 165 | | | | | 170 | | | | | 175 | | |
| AGC | ACG | CAA | GGC | CAA | GGA | GGT | CCT | CCC | AGC | CAT | CCG | AGG | CTA | GCT | GCA | 576 |
| Ser | Thr | Gln | Gly | Gln | Gly | Gly | Pro | Pro | Ser | His | Pro | Arg | Leu | Ala | Ala | |
| | | | 180 | | | | | 185 | | | | | 190 | | | |
| CTA | CTT | CTT | CGG | CTG | CCG | AGA | CTG | CGC | AAG | CCA | CTT | CGA | GCA | GAT | GCT | 624 |
| Leu | Leu | Leu | Arg | Leu | Pro | Arg | Leu | Arg | Lys | Pro | Leu | Arg | Ala | Asp | Ala | |
| | | 195 | | | | | 200 | | | | | 205 | | | | |

FIG. 1B

| | | | | | | | | | | | | | | | | |
|---|---|---|---|---|---|---|---|---|---|---|---|---|---|---|---|---|
| GCT | GCC | TCC | ATG | CAC | CGG | GTG | GGG | AGT | CCC | AAC | GCC | GCT | GTC | CTC | TGG | 672 |
| Ala | Ala | Ser | Met | His | Arg | Val | Gly | Ser | Pro | Asn | Ala | Ala | Val | Leu | Trp | |
| | | | 210 | | | | 215 | | | | 220 | | | | | |
| CTC | TGG | TCT | AGC | CAC | AAC | AGG | GTC | AAT | GCT | CGC | TTG | CAG | GTG | CCC | CCA | 720 |
| Leu | Trp | Ser | Ser | His | Asn | Arg | Val | Asn | Ala | Arg | Leu | Gln | Val | Pro | Pro | |
| 225 | | | | 230 | | | | | 235 | | | | | 240 | | |
| GCG | AGG | ACC | CCC | AGT | TCC | CCA | AGG | TGC | AGT | GGC | CAC | CCC | GTG | AAC | TTT | 768 |
| Ala | Arg | Thr | Pro | Ser | Ser | Pro | Arg | Cys | Ser | Gly | His | Pro | Val | Asn | Phe | |
| | | | | 245 | | | | | 250 | | | | | 255 | | |
| GTT | CTG | CCT | GCC | ACA | ATG | AAC | GCC | TGG | ATG | TGC | CCG | TGT | GGG | ACG | TGG | 816 |
| Val | Leu | Pro | Ala | Thr | Met | Asn | Ala | Trp | Met | Cys | Pro | Cys | Gly | Thr | Trp | |
| | | | | 260 | | | | | 265 | | | | 270 | | | |
| AAG | CCA | CCC | TCA | ACT | TCC | TCA | AGG | CCC | ACT | TCT | CCC | CAA | GCA | ACA | TCA | 864 |
| Lys | Pro | Pro | Ser | Thr | Ser | Ser | Arg | Pro | Thr | Ser | Pro | Gln | Ala | Thr | Ser | |
| | | 275 | | | | | 280 | | | | | 285 | | | | |
| TCC | TGG | ACT | TCC | CTG | CAG | CTG | GGT | CAG | CTG | CCG | GAG | GGA | TGT | GCA | GAA | 912 |
| Ser | Trp | Thr | Ser | Leu | Gln | Leu | Gly | Gln | Leu | Pro | Glu | Gly | Cys | Ala | Glu | |
| | 290 | | | | | 295 | | | | | 300 | | | | | |
| TGT | GCA | GCC | GCC | CCA | GAG | CTG | GCG | ATG | GGA | GCC | CTG | GAG | CTG | GAA | AGC | 960 |
| Cys | Ala | Ala | Ala | Pro | Glu | Leu | Ala | Met | Gly | Ala | Leu | Glu | Leu | Glu | Ser | |
| 305 | | | | | 310 | | | | | 315 | | | | | 320 | |
| CGG | AAT | TCA | ACT | CTG | GAC | CCT | GGG | AAG | CCT | GAG | ATG | ATG | AAG | TCC | CCC | 1008 |
| Arg | Asn | Ser | Thr | Leu | Asp | Pro | Gly | Lys | Pro | Glu | Met | Met | Lys | Ser | Pro | |
| | | | | 325 | | | | | 330 | | | | | 335 | | |
| ACA | AAC | ACC | ACC | CCA | CAT | GTG | CCG | GCT | GAG | GGA | CCT | GAG | GCA | AGT | CGA | 1056 |
| Thr | Asn | Thr | Thr | Pro | His | Val | Pro | Ala | Glu | Gly | Pro | Glu | Ala | Ser | Arg | |
| | | | 340 | | | | | 345 | | | | | 350 | | | |
| CCC | CCG | AAG | CTG | CAC | CCT | GGC | CTC | AGA | GCT | GCA | CCA | GGC | CAG | GAG | CCT | 1104 |
| Pro | Pro | Lys | Leu | His | Pro | Gly | Leu | Arg | Ala | Ala | Pro | Gly | Gln | Glu | Pro | |
| | | 355 | | | | | 360 | | | | | 365 | | | | |
| CCT | GAG | CAC | ATG | GCA | GAC | GTT | CAG | AGG | AAT | GAG | CAG | GAC | GAG | CCG | CTT | 1152 |
| Pro | Glu | His | Met | Ala | Asp | Val | Gln | Arg | Asn | Glu | Gln | Asp | Glu | Pro | Leu | |
| | 370 | | | | | 375 | | | | | 380 | | | | | |
| GGG | CAG | TGG | CAC | TTA | CGA | AGC | GAG | ACA | CAG | GGG | CTG | CAT | TGC | TGG | CTG | 1200 |
| Gly | Gln | Trp | His | Leu | Arg | Ser | Glu | Thr | Gln | Gly | Leu | His | Cys | Trp | Leu | |
| 385 | | | | | 390 | | | | | 395 | | | | | 400 | |
| AGT | CCA | GGG | CTG | AGA | AGA | ACC | GCC | TCT | GGG | GCC | CTT | TGG | AGG | TCA | GGC | 1248 |
| Ser | Pro | Gly | Leu | Arg | Arg | Thr | Ala | Ser | Gly | Ala | Leu | Trp | Arg | Ser | Gly | |
| | | | | 405 | | | | | 410 | | | | | 415 | | |
| GCG | TGG | GCC | GCA | GCT | CCA | AGC | AGC | TGG | TCG | ACA | TCC | CTG | AGG | CCA | GCT | 1296 |

FIG. 1C

```
                Ala Trp Ala Ala Ala Pro Ser Ser Trp Ser Thr Ser Leu Arg Pro Ala
                            420                 425                 430
GGA GGC CCG AGC TGG ACG GGC CGA GGC CAG TGG CTG CAG GTG CTG GGA                    1344
Gly Gly Pro Ser Trp Thr Gly Arg Gly Gln Trp Leu Gln Val Leu Gly
            435                 440                 445
GGG GGC TTC TCT TAC CTG GAC ATC AGC CTC TGT GTG GGG CTC TAT CCC                    1392
Gly Gly Phe Ser Tyr Leu Asp Ile Ser Leu Cys Val Gly Leu Tyr Pro
        450                 455                 460
TGT CCT TCA TGG GCC TGC TGG CAT GTA CAC CTA CTT CCA GGC CAA GAT                    1440
Cys Pro Ser Trp Ala Cys Trp His Val His Leu Leu Pro Gly Gln Asp
465                 470                 475                 480
AAG GCC CTG AAC CGG ATG CTG GCC ACC CTG CAG CCT GAA CCA CCT GGG                    1488
Lys Ala Leu Asn Arg Met Leu Ala Thr Leu Gln Pro Glu Pro Pro Gly
                    485                 490                 495
GAG GAG GCG GGA GAG GGA GCT GCC ATC TCT AGG CAC CTC AAG CCC CCT                    1536
Glu Glu Ala Gly Glu Gly Ala Ala Ile Ser Arg His Leu Lys Pro Pro
                500                 505                 510
GAC CCC ATT CCC TCC CCT CCC ACC CCT TGC TCC TTG TCT GGC CTA GAA                    1584
Asp Pro Ile Pro Ser Pro Pro Thr Pro Cys Ser Leu Ser Gly Leu Glu
            515                 520                 525
GTG TGG GAA ATT CAG GAA AAC GAG TTG CTC CAG                                        1617
Val Trp Glu Ile Gln Glu Asn Glu Leu Leu Gln
        530                 535
```

FIG. 2A

```
ATG AGG AGG TGC AAC AGC GGC TCC GGG CCG CCG CCG TCG CTG CTG CTG        48
Met Arg Arg Cys Asn Ser Gly Ser Gly Pro Pro Pro Ser Leu Leu Leu
 1               5                  10                  15

CTG CTG CTG TGG CTG CTC GCG GTT CCC GGC GCT AAC GCG GCC CCG CGG        96
Leu Leu Leu Trp Leu Leu Ala Val Pro Gly Ala Asn Ala Ala Pro Arg
            20                  25                  30

TCG GCG CTC TAT TCG CCT TCC GAC CCG CTG ACG CTG CTG CAG GCG GAC       144
Ser Ala Leu Tyr Ser Pro Ser Asp Pro Leu Thr Leu Leu Gln Ala Asp
        35                  40                  45

ACG GTG CGC GGC GCG GTG CTG GGC TCC CGC AGC GCC TGG GCC GTG GAG       192
Thr Val Arg Gly Ala Val Leu Gly Ser Arg Ser Ala Trp Ala Val Glu
    50                  55                  60

TTC TTC GCC TCC TGG TGC GGC CAC TGC ATC GCC TTC GCC CCG ACG TGG       240
Phe Phe Ala Ser Trp Cys Gly His Cys Ile Ala Phe Ala Pro Thr Trp
65                  70                  75                  80

AAG GCG CTG GCC GAA GAC GTC AAA GCC TGG AGG CCG GCC CTG TAT CTC       288
Lys Ala Leu Ala Glu Asp Val Lys Ala Trp Arg Pro Ala Leu Tyr Leu
                85                  90                  95

GCC GCC CTG GAC TGT GCT GAG GAG ACC AAC AGT GCA GTC TGC AGA GAC       336
Ala Ala Leu Asp Cys Ala Glu Glu Thr Asn Ser Ala Val Cys Arg Asp
            100                 105                 110

TTC AAC ATC CCT GGC TTC CCG ACT GTG AGG TTC TTC AAG GCC TTT ACC       384
Phe Asn Ile Pro Gly Phe Pro Thr Val Arg Phe Phe Lys Ala Phe Thr
        115                 120                 125

AAG AAC GGC TCG GGA GCA GTA TTT CCA GTG GCT GGT GCT GAC GTG CAG       432
Lys Asn Gly Ser Gly Ala Val Phe Pro Val Ala Gly Ala Asp Val Gln
    130                 135                 140

ACG CTG CGG GAG AGG CTC ATT GAC GCC CTG GAG TCC CAT CAT GAC ACG       480
Thr Leu Arg Glu Arg Leu Ile Asp Ala Leu Glu Ser His His Asp Thr
145                 150                 155                 160

TGG CCC CCA GCC TGT CCC CCA CTG GAG CCT GCC AAG CTG GAG GAG ATT       528
Trp Pro Pro Ala Cys Pro Pro Leu Glu Pro Ala Lys Leu Glu Glu Ile
                165                 170                 175

GAT GGA TTC TTT GCG AGA AAT AAC GAA GAG TAC CTG GCT CTG ATC TTT       576
Asp Gly Phe Phe Ala Arg Asn Asn Glu Glu Tyr Leu Ala Leu Ile Phe
            180                 185                 190

GAA AAG GGA GGC TCC TAC CTG GGT AGA GAG GTG GCT CTG GAC CTG TCC       624
Glu Lys Gly Gly Ser Tyr Leu Gly Arg Glu Val Ala Leu Asp Leu Ser
        195                 200                 205
```

FIG. 2B

| | | |
|---|---|---|
| CAG CAC AAA GGC GTG GCG GTG CGC AGG GTG CTG AAC ACA GAG GCC AAT<br>Gln His Lys Gly Val Ala Val Arg Arg Val Leu Asn Thr Glu Ala Asn<br>     210                     215                    220 | 672 |
| GTG GTG AGA AAG TTT GGT GTC ACC GAC TTC CCC TCT TGC TAC CTG CTG<br>Val Val Arg Lys Phe Gly Val Thr Asp Phe Pro Ser Cys Tyr Leu Leu<br>225                   230                  235                   240 | 720 |
| TTC CGG AAT GGC TCT GTC TCC CGA GTC CCC GTG CTC ATG GAA TCC AGG<br>Phe Arg Asn Gly Ser Val Ser Arg Val Pro Val Leu Met Glu Ser Arg<br>                   245                  250                  255 | 768 |
| TCC TTC TAT ACC GCT TAC CTG CAG AGA CTC TCT GGG CTC ACC AGG GAG<br>Ser Phe Tyr Thr Ala Tyr Leu Gln Arg Leu Ser Gly Leu Thr Arg Glu<br>              260                  265                    270 | 816 |
| GCT GCC CAG ACC ACA GTT GCA CCA ACC ACT GCT AAC AAG ATA GCT CCC<br>Ala Ala Gln Thr Thr Val Ala Pro Thr Thr Ala Asn Lys Ile Ala Pro<br>         275                    280                  285 | 864 |
| ACT GTT TGG AAA TTG GCA GAT CGC TCC AAG ATC TAC ATG GCT GAC CTG<br>Thr Val Trp Lys Leu Ala Asp Arg Ser Lys Ile Tyr Met Ala Asp Leu<br>290                   295                   300 | 912 |
| GAA TCT GCA CTG CAC TAC ATC CTG CGG ATA GAA GTG GGC AGG TTC CCG<br>Glu Ser Ala Leu His Tyr Ile Leu Arg Ile Glu Val Gly Arg Phe Pro<br>305                   310                  315              320 | 960 |
| GTC CTG GAA GGG CAG CGC CTG GTG GCC CTG AAA AAG TTT GTG GCA GTG<br>Val Leu Glu Gly Gln Arg Leu Val Ala Leu Lys Lys Phe Val Ala Val<br>                   325                  330                  335 | 1008 |
| CTG GCC AAG TAT TTC CCT GGC CGG CCC TTA GTC CAG AAC TTC CTG CAC<br>Leu Ala Lys Tyr Phe Pro Gly Arg Pro Leu Val Gln Asn Phe Leu His<br>              340                  345                    350 | 1056 |
| TCC GTG AAT GAA TGG CTC AAG AGG CAG AAG AGA AAT AAA ATT CCC TAC<br>Ser Val Asn Glu Trp Leu Lys Arg Gln Lys Arg Asn Lys Ile Pro Tyr<br>         355                    360                  365 | 1104 |
| AGT TTC TTT AAA ACT GCC CTG GAC GAC AGG AAA GAG GGT GCC GTT CTT<br>Ser Phe Phe Lys Thr Ala Leu Asp Asp Arg Lys Glu Gly Ala Val Leu<br>370                   375                   380 | 1152 |
| GCC AAG AAG GTG AAC TGG ATT GGC TGC CAG GGG AGT GAG CCG CAT TTC<br>Ala Lys Lys Val Asn Trp Ile Gly Cys Gln Gly Ser Glu Pro His Phe<br>385                   390                  395              400 | 1200 |
| CGG GGC TTT CCC TGC TCC CTG TGG GTC CTC TTC CAC TTC TTG ACT GTG<br>Arg Gly Phe Pro Cys Ser Leu Trp Val Leu Phe His Phe Leu Thr Val<br>                   405                  410                  415 | 1248 |
| CAG GCA GCT CGC CAA AAT GTA GAC CAC TCA CAG GAA GCA GCC AAG GCC | 1296 |

FIG. 2C

| | |
|---|---|
| Gln Ala Ala Arg Gln Asn Val Asp His Ser Gln Glu Ala Ala Lys Ala<br>420 425 430 | |
| AAG GAG GTC CTC CCA GCC ATC CGA GGC TAC GTG CAC TAC TTC TTC GGC<br>Lys Glu Val Leu Pro Ala Ile Arg Gly Tyr Val His Tyr Phe Phe Gly<br>435 440 445 | 1344 |
| TGC CGA GAC TGC GCT AGC CAC TTC GAG CAG ATG GCT GCT GCC TCC ATG<br>Cys Arg Asp Cys Ala Ser His Phe Glu Gln Met Ala Ala Ala Ser Met<br>450 455 460 | 1392 |
| CAC CGG GTG GGG AGT CCC AAC GCC GCT GTC CTC TGG CTC TGG TCT AGC<br>His Arg Val Gly Ser Pro Asn Ala Ala Val Leu Trp Leu Trp Ser Ser<br>465 470 475 480 | 1440 |
| CAC AAC AGG GTC AAT GCT CGC CTT GCA GGT GCC CCC AGC GAG GAC CCC<br>His Asn Arg Val Asn Ala Arg Leu Ala Gly Ala Pro Ser Glu Asp Pro<br>485 490 495 | 1488 |
| CAG TTC CCC AAG GTG CAG TGG CCA CCC CGT GAA CTT TGT TCT GCC TGC<br>Gln Phe Pro Lys Val Gln Trp Pro Pro Arg Glu Leu Cys Ser Ala Cys<br>500 505 510 | 1536 |
| CAC AAT GAA CGC CTG GAT GTG CCC GTG TGG GAC GTG GAA GCC ACC CTC<br>His Asn Glu Arg Leu Asp Val Pro Val Trp Asp Val Glu Ala Thr Leu<br>515 520 525 | 1584 |
| AAC TTC CTC AAG GCC CAC TTC TCC CCA AGC AAC ATC ATC CTG GAC TTC<br>Asn Phe Leu Lys Ala His Phe Ser Pro Ser Asn Ile Ile Leu Asp Phe<br>530 535 540 | 1632 |
| CCT GCA GCT GGG TCA GCT GCC CGG AGG GAT GTG CAG AAT GTG GCA GCC<br>Pro Ala Ala Gly Ser Ala Ala Arg Arg Asp Val Gln Asn Val Ala Ala<br>545 550 555 560 | 1680 |
| GCC CCA GAG CTG GCG ATG GGA GCC CTG GAG CTG GAA AGC CGG AAT TCA<br>Ala Pro Glu Leu Ala Met Gly Ala Leu Glu Leu Glu Ser Arg Asn Ser<br>565 570 575 | 1728 |
| ACT CTG GAC CCT GGG AAG CCT GAG ATG ATG AAG TCC CCC ACA AAC ACC<br>Thr Leu Asp Pro Gly Lys Pro Glu Met Met Lys Ser Pro Thr Asn Thr<br>580 585 590 | 1776 |
| ACC CCA CAT GTG CCG GCT GAG GGA CCT GAG CTT ATT<br>Thr Pro His Val Pro Ala Glu Gly Pro Glu Leu Ile<br>595 600 | 1812 |

FIG. 3A

| | |
|---|---|
| ATG AGG AGG TGC AAC AGC GGC TCC GGG CCG CCG CCG TCG CTG CTG CTG<br>Met Arg Arg Cys Asn Ser Gly Ser Gly Pro Pro Pro Ser Leu Leu Leu<br>1                         5                            10                         15 | 48 |
| CTG CTG CTG TGG CTG CTC GCG GTT CCC GGC GCT AAC GCG GCC CCG CGG<br>Leu Leu Leu Trp Leu Leu Ala Val Pro Gly Ala Asn Ala Ala Pro Arg<br>                  20                           25                         30 | 96 |
| TCG GCG CTC TAT TCG CCT TCC GAC CCG CTG ACG CTG CTG CAG GCG GAC<br>Ser Ala Leu Tyr Ser Pro Ser Asp Pro Leu Thr Leu Leu Gln Ala Asp<br>         35                         40                           45 | 144 |
| ACG GTG CGC GGC GCG GTG CTG GGC TCC CGC AGC GCC TGG GCC GTG GAG<br>Thr Val Arg Gly Ala Val Leu Gly Ser Arg Ser Ala Trp Ala Val Glu<br>    50                        55                        60 | 192 |
| TTC TTC GCC TCC TGG TGC GGC CAC TGC ATC GCC TTC GCC CCG ACG TGG<br>Phe Phe Ala Ser Trp Cys Gly His Cys Ile Ala Phe Ala Pro Thr Trp<br>65                        70                         75                      80 | 240 |
| AAG GCG CTG GCC GAA GAC GTC AAA GCC TGG AGG CCG GCC CTG TAT CTC<br>Lys Ala Leu Ala Glu Asp Val Lys Ala Trp Arg Pro Ala Leu Tyr Leu<br>                  85                           90                         95 | 288 |
| GCC GCC CTG GAC TGT GCT GAG GAG ACC AAC AGT GCA GTC TGC AGA GAC<br>Ala Ala Leu Asp Cys Ala Glu Glu Thr Asn Ser Ala Val Cys Arg Asp<br>              100                         105                      110 | 336 |
| TTC AAC ATC CCT GGC TTC CCG ACT GTG AGG TTC TTC AAG GCC TTT ACC<br>Phe Asn Ile Pro Gly Phe Pro Thr Val Arg Phe Phe Lys Ala Phe Thr<br>          115                         120                      125 | 384 |
| AAG AAC GGC TCG GGA GCA GTA TTT CCA GTG GCT GGT GCT GAC GTG CAG<br>Lys Asn Gly Ser Gly Ala Val Phe Pro Val Ala Gly Ala Asp Val Gln<br>       130                         135                         140 | 432 |
| ACG CTG CGG GAG AGG CTC ATT GAC GCC CTG GAG TCC CAT CAT GAC ACG<br>Thr Leu Arg Glu Arg Leu Ile Asp Ala Leu Glu Ser His His Asp Thr<br>145                         150                         155                     160 | 480 |
| TGG CCC CCA GCC TGT CCC CCA CTG GAG CCT GCC AAG CTG GAG GAG ATT<br>Trp Pro Pro Ala Cys Pro Pro Leu Glu Pro Ala Lys Leu Glu Glu Ile<br>              165                        170                      175 | 528 |
| GAT GGA TTC TTT GCG AGA AAT AAC GAA GAG TAC CTG GCT CTG ATC TTT<br>Asp Gly Phe Phe Ala Arg Asn Asn Glu Glu Tyr Leu Ala Leu Ile Phe<br>          180                        185                     190 | 576 |
| GAA AAG GGA GGC TCC TAC CTG GGT AGA GAG GTG GCT CTG GAC CTG TCC<br>Glu Lys Gly Gly Ser Tyr Leu Gly Arg Glu Val Ala Leu Asp Leu Ser<br>       195                         200                     205 | 624 |

FIG. 3B

```
CAG CAC AAA GGC GTG GCG GTG CGC AGG GTG CTG AAC ACA GAG GCC AAT      672
Gln His Lys Gly Val Ala Val Arg Arg Val Leu Asn Thr Glu Ala Asn
    210             215                 220

GTG GTG AGA AAG TTT GGT GTC ACC GAC TTC CCC TCT TGC TAC CTG CTG      720
Val Val Arg Lys Phe Gly Val Thr Asp Phe Pro Ser Cys Tyr Leu Leu
225             230                 235                 240

TTC CGG AAT GGC TCT GTC TCC CGA GTC CCC GTG CTC ATG GAA TCC AGG      768
Phe Arg Asn Gly Ser Val Ser Arg Val Pro Val Leu Met Glu Ser Arg
                245                 250                 255

TCC TTC TAT ACC GCT TAC CTG CAG AGA CTC TCT GGG CTC ACC AGG GAG      816
Ser Phe Tyr Thr Ala Tyr Leu Gln Arg Leu Ser Gly Leu Thr Arg Glu
            260                 265                 270

GCT GCC CAG ACC ACA GTT GCA CCA ACC ACT GCT AAC AAG ATA GCT CCC      864
Ala Ala Gln Thr Thr Val Ala Pro Thr Thr Ala Asn Lys Ile Ala Pro
        275                 280                 285

ACT GTT TGG AAA TTG GCA GAT CGC TCC AAG ATC TAC ATG GCT GAC CTG      912
Thr Val Trp Lys Leu Ala Asp Arg Ser Lys Ile Tyr Met Ala Asp Leu
    290                 295                 300

GAA TCT GCA CTG CAC TAC ATC CTG CGG ATA GAA GTG GGC AGG TTC CCG      960
Glu Ser Ala Leu His Tyr Ile Leu Arg Ile Glu Val Gly Arg Phe Pro
305             310                 315                 320

GTC CTG GAA GGG CAG CGC CTG GTG GCC CTG AAA AAG TTT GTG GCA GTG     1008
Val Leu Glu Gly Gln Arg Leu Val Ala Leu Lys Lys Phe Val Ala Val
                325                 330                 335

CTG GCC AAG TAT TTC CCT GGC CGG CCC TTA GTC CAG AAC TTC CTG CAC     1056
Leu Ala Lys Tyr Phe Pro Gly Arg Pro Leu Val Gln Asn Phe Leu His
            340                 345                 350

TCC GTG AAT GAA TGG CTC AAG AGG CAG AAG AGA AAT AAA ATT CCC TAC     1104
Ser Val Asn Glu Trp Leu Lys Arg Gln Lys Arg Asn Lys Ile Pro Tyr
        355                 360                 365

AGT TTC TTT AAA ACT GCC CTG GAC GAC AGG AAA GAG GGT GCC GTT CTT     1152
Ser Phe Phe Lys Thr Ala Leu Asp Asp Arg Lys Glu Gly Ala Val Leu
    370                 375                 380

GCC AAG AAG GTG AAC TGG ATT GGC TGC CAG GGG AGT GAG CCG CAT TTC     1200
Ala Lys Lys Val Asn Trp Ile Gly Cys Gln Gly Ser Glu Pro His Phe
385             390                 395                 400

CGG GGC TTT CCC TGC TCC CTG TGG GTC CTC TTC CAC TTC TTG ACT GTG     1248
Arg Gly Phe Pro Cys Ser Leu Trp Val Leu Phe His Phe Leu Thr Val
                405                 410                 415

CAG GCA GCT CGC CAA AAT GTA GAC CAC TCA CAG GAA GCA GCC AAG GCC     1296
```

FIG. 3C

|  |  |
|---|---|
| Gln Ala Ala Arg Gln Asn Val Asp His Ser Gln Glu Ala Ala Lys Ala<br>            420                  425                  430 |  |
| AAG GAG GTC CTC CCA GCC ATC CGA GGC TAC GTG CAC TAC TTC TTC GGC<br>Lys Glu Val Leu Pro Ala Ile Arg Gly Tyr Val His Tyr Phe Phe Gly<br>        435                  440                445 | 1344 |
| TGC CGA GAC TGC GCT AGC CAC TTC GAG CAG ATG GCT GCT GCC TCC ATG<br>Cys Arg Asp Cys Ala Ser His Phe Glu Gln Met Ala Ala Ala Ser Met<br>    450                  455                460 | 1392 |
| CAC CGG GTG GGG AGT CCC AAC GCC GCT GTC CTC TGG CTC TGG TCT AGC<br>His Arg Val Gly Ser Pro Asn Ala Ala Val Leu Trp Leu Trp Ser Ser<br>465                  470                  475                480 | 1440 |
| CAC AAC AGG GTC AAT GCT CGC CTT GCA GGT GCC CCC AGC GAG GAC CCC<br>His Asn Arg Val Asn Ala Arg Leu Ala Gly Ala Pro Ser Glu Asp Pro<br>            485                  490                495 | 1488 |
| CAG TTC CCC AAG GTG CAG TGG CCA CCC CGT GAA CTT TGT TCT GCC TGC<br>Gln Phe Pro Lys Val Gln Trp Pro Pro Arg Glu Leu Cys Ser Ala Cys<br>        500                  505                510 | 1536 |
| CAC AAT GAA CGC CTG GAT GTG CCC GTG TGG GAC GTG GAA GCC ACC CTC<br>His Asn Glu Arg Leu Asp Val Pro Val Trp Asp Val Glu Ala Thr Leu<br>        515                  520                525 | 1584 |
| AAC TTC CTC AAG GCC CAC TTC TCC CCA AGC AAC ATC ATC CTG GAC TTC<br>Asn Phe Leu Lys Ala His Phe Ser Pro Ser Asn Ile Ile Leu Asp Phe<br>        530                  535                540 | 1632 |
| CCT GCA GCT GGG TCA GCT GCC CGG AGG GAT GTG CAG AAT GTG GCA GCC<br>Pro Ala Ala Gly Ser Ala Ala Arg Arg Asp Val Gln Asn Val Ala Ala<br>545                  550                  555                560 | 1680 |
| GCC CCA GAG CTG GCG ATG GGA GCC CTG GAG CTG GAA AGC CGG AAT TCA<br>Ala Pro Glu Leu Ala Met Gly Ala Leu Glu Leu Glu Ser Arg Asn Ser<br>            565                  570                575 | 1728 |
| ACT CTG GAC CCT GGG AAG CCT GAG ATG ATG AAG TCC CCC ACA AAC ACC<br>Thr Leu Asp Pro Gly Lys Pro Glu Met Met Lys Ser Pro Thr Asn Thr<br>            580                  585                590 | 1776 |
| ACC CCA CAT GTG CCG GCT GAG GGA CCT GAG GCA AGT CGA CCC CCG AAG<br>Thr Pro His Val Pro Ala Glu Gly Pro Glu Ala Ser Arg Pro Pro Lys<br>        595                  600                605 | 1824 |
| CTG CAC CCT GGC CTC AGA GCT GCA CCA GGC CAG GAG CCT CCT GAG CAC<br>Leu His Pro Gly Leu Arg Ala Ala Pro Gly Gln Glu Pro Pro Glu His<br>        610                  615                620 | 1872 |
| ATG GCA GAG CTT CAG AGG AAT GAG CAG GAG CAG CCG CTT GGG CAG TGG<br>Met Ala Glu Leu Gln Arg Asn Glu Gln Glu Gln Pro Leu Gly Gln Trp<br>625                  630                  635                640 | 1920 |

FIG. 3D

```
CAC TTG AGC AAG CGA GAC ACA GGG GCT GCA TTG CTG GCT GAG TCC AGG      1968
His Leu Ser Lys Arg Asp Thr Gly Ala Ala Leu Leu Ala Glu Ser Arg
            645                 650                 655

GCT GAG AAG AAC CGC CTC TGG GGC CCT TTG GAG GTC AGG CGC GTG GGC      2016
Ala Glu Lys Asn Arg Leu Trp Gly Pro Leu Glu Val Arg Arg Val Gly
            660                 665                 670

CGC AGC TCC AAG CAG CTG GTC GAC ATC CCT GAG GGC CAG CTG GAG GCC      2064
Arg Ser Ser Lys Gln Leu Val Asp Ile Pro Glu Gly Gln Leu Glu Ala
            675                 680                 685

CGA GCT GGA CGG GGC CGA GGC CAG TGG CTG CAG CTT ATT                  2103
Arg Ala Gly Arg Gly Arg Gly Gln Trp Leu Gln Leu Ile
    690                 695                 700
```

METHOD FOR PROMOTING CELL PROLIFERATION AND GROWTH

This application is a division of application Ser. No. 08/735,041, filed Oct. 22, 1996, now U.S. Pat. No. 5,914,251.

FIELD OF THE INVENTION

This invention relates in general to polypeptides with growth promoting activities. More specifically, the invention concerns: growth factors (herein termed placental-derived prostate factors, or "PDPFs"), having the ability to stimulate the proliferation and growth of prostate cells and other cells; recombinant methods for the production of such growth factors; methods for the use of such growth factors to stimulate cell proliferation, growth and/or survival; diagnostic methods for the detection of such factors in biological samples by the use of PDPF antibodies and labeled nucleic acid probes; and methods for the identification of inhibitors against PDPF that will be potentially useful as anti-cancer agents.

BACKGROUND OF THE INVENTION

It has been estimated that each year, nearly two hundred and fifty thousand men in the United States are diagnosed with prostate cancer and that approximately forty thousand men will die from it; Boring et al., CA Cancer Journal for Clinicians, Volume 44, Number 1, pages 7–26 (1994). Current treatments, which include surgery, radiation and hormone ablation, have some effect on slowing tumor growth but show no significant effect on long term remission or cure; Scher, Current Opinion in Oncology, Volume 3, pages 568–574 (1991). When confined within the organ capsule, prostate carcinoma is relatively easy to treat successfully. However, metastatic disease, which targets to the axial skeleton about eighty percent of the time, is nearly always refractory to treatment; Franks, Journal of Pathology and Bacteriology, Volume 72, pages 603–611 (1956); and Huben et al., CA Cancer Journal for Clinicians., Volume 36, Number 5, pages 274–292 (1986).

The dissemination of prostate carcinoma cells to the bones of the central spine has been ascribed to the presence of paravertebral vessels; Zetter et al., Prostate Cancer and Bone Metastasis, edited by Karr and Yamanaka, Plenum Press, New York (1992), at pages 39–43. However, this direct metastatic route does not explain why the level of tumor cell proliferation in bone is often higher than in the prostate gland itself; Jacobs, Urology, Volume 21, Number 4, pages 337–344 (1983). Additionally, bone metastases are often the first evidence of progression to androgen-independent prostate carcinoma; Logothetis et al., Seminars in Oncology, Volume 21, Number 5, pages 620–629 (1994). The uncoupling of prostate carcinoma cell growth from hormone responsiveness signals the failure or irrelevance of hormone ablation therapy and the increasing ability of prostate carcinoma cells to proliferate in response to paracrine and autocrine peptide growth factors; Thompson, Cancer Cells, Volume 2, Number 11, pages 345–354 (1990); and Scher et al., Seminars in Urology, Volume 10, Number 1, pages 55–64 (1992). Although clinical relevance has not been convincingly established, several growth factors, including bFGF, aFGF, EGF, TGFa, and PDGF, have been isolated from the conditioned media of human prostate carcinoma cells in vitro, and from prostate tissue in vivo.

Bone stromal cells also produce factors that stimulate the proliferation of prostate carcinoma cells; Chackal-Roy et al., Journal of Clinical Investigation, Volume 84, pages 43–50 (1989). The interactions of prostate stromal and epithelial cells with regard to KGF and bFGF have been well established; Chung, Cancer Biology, Volume 4, pages 183–192 (1993). However, the interactions between bone stromal cells and metastatic prostate carcinoma cells has not yet been studied as closely. Conditioned media from bone stromal cells, but not skeletal muscle, keratinocytes or kidney epithelial cells, stimulates the proliferation of prostate carcinoma cells; see Zetter et al. above. Furthermore, bone stromal cell media is not active on kidney carcinoma or melanoma cells, suggesting tissue specific interactions between bone stromal cells and prostate carcinoma cells. This tissue specificity has been confirmed in vivo by co-inoculating stromal cells and LNCaP prostate carcinoma cells, which are normally non-tumorigenic, into nude mice; Gleave et al., Cancer Research, Volume 51, pages 3753–3761 (1991). In these studies, bone or prostate stromal cells supported tumor growth in vivo, whereas lung or kidney stromal cells did not.

One factor, identified in bone stromal cell cultures, that stimulates prostate cell proliferation is transferrin, which is a well-characterized protein involved in the transport of iron across cell membranes; Rossi et al., Proceedings of the National Academy of Science U.S.A., Volume 89, pages 6197–6201 (1992). In addition, published PCT patent application PCT/US95/09261 (WO 96/04379) describes the isolation and expression of DNA encoding a bone and prostate-derived growth factor, termed BPGF-1. The BPGF-1 gene was found to be expressed predominantly in bone, prostate tissue and seminal vesicles, and BPGF-1 polypeptide stimulated the proliferation of prostatic epithelial cells in vitro.

SUMMARY OF THE INVENTION

The present invention provides novel growth factors which stimulate the growth of prostate and other cell types, and which are distinct from BPGF-1. The growth factors of this invention are polypeptides (i.e., proteins) that stimulate the proliferation of several prostate carcinoma cell lines, but not normal prostate epithelial cells. In addition, the growth of other tumor cells derived from placenta, oral epithelium, palate and bone is also stimulated. The growth factors of this invention are herein individually and collectively termed "placenta-derived prostate factor", or "PDPF", based on the tissue origin of the cDNA library used to clone the encoding nucleic acid molecules and the fact that these factors have activity against prostate cells. Of two variably spliced forms specifically identified so far, the shorter polypeptide form (termed PDPF-1) appears to be more active in the cell growth assays evaluated.

The present invention also encompasses genes and nucleic acid molecules that encode such polypeptides, as well as recombinant methods for the use of the genes and nucleic acid molecules to produce the polypeptides. Additionally, this invention is directed to the use of the polypeptides to promote the growth of prostate and other cells responsive to the growth promoting effects of the polypeptides, either in vitro or in vivo. The protein growth factors of this invention can also be used in assays and screens for the identification of antagonists, i.e., inhibitors of PDPF cell proliferation stimulating activity, such antagonists being potentially useful as anti-tumor agents for the treatment of responsive tumors. The invention is further concerned with the use of PDPF antibodies and nucleic acid molecules encoding PDPF, or fragments (i.e., segments) thereof, in diagnostic methods for the detection of PDPF in biological samples such as tissue or fluid samples, including their use in diagnostic methods for the detection of tumors.

Especially preferred embodiments of this invention are nucleic acid molecules having the DNA sequences of SEQ ID NOS: 3 or 5, and proteins having the amino acid sequences of SEQ ID NOS: 4 or 6. Also preferred is an alternative nucleic acid sequence to the one of SEQ ID NO: 5, in which the base "C" at position 1260 is changed to "G" (but otherwise encoding the same polypeptide) (SEQ ID NO: 7). In addition to these preferred embodiments, the invention also encompasses fragments (such as truncation analogs or interior segments of the proteins) and other derivative molecules of modified sequence, including substitution, deletion and addition analogs, having the growth promoting activity of the full length sequence of PDPF, as will be more fully described in the following text.

The terms "gene", "DNA", and "nucleic acid molecule" used herein with reference to this invention are meant to refer to isolated molecules that are free of total genomic DNA of a particular species, while retaining coding sequences for the described polypeptides.

BRIEF DESCRIPTION OF THE FIGURES

FIGS. 1A–1C. These figures show the DNA sequence (SEQ ID NO: 1) and predicted amino acid sequence (SEQ ID NO: 2) of the polypeptide known as BPGF-1, as disclosed in the above mentioned WO 96/04379.

FIGS. 2A–2C. These figures show the DNA sequence (SEQ ID NO: 3) and predicted amino acid sequence (SEQ ID NO: 4) of a growth promoting polypeptide (PDPF-1) in accordance with the present invention.

FIGS. 3A–3D. These figures show the DNA sequence (SEQ ID NO: 5) and predicted amino acid sequence (SEQ ID NO: 6) of another growth promoting polypeptide (PDPF-2) in accordance with the present invention.

(FIGS. 4E, 4F, and 4G).

DETAILED DESCRIPTION OF THE INVENTION

Figure 4A:
FIGS. 4A–4G. These figures show the results of an analysis of various tissue sections taken from normal embryonic and adult rats, using for the analysis a DNA probe for PDPF mRNA that had been radiolabeled with $^{33}$P. As shown in the figure, many structures in the embryo (FIG. 4A) express mRNA for PDPF, including kidney, pancreas, heart and skin. There is also strong signal in the chorionic plate and the maternal tissue of the placenta. In the adult male reproductive tract, the epididymal epithelia (middle row, FIG. 4B) express mRNA for PDPF, the seminiferous tubules (middle row, FIG. 4C) express varying amounts of mRNA for PDPF, and the vesicular gland epithelia (middle row, FIG. 4D) demonstrated the highest level of expression of mRNA for PDPF. Bright field images of the middle row panels are adjacent on the right.
Figure 4B:
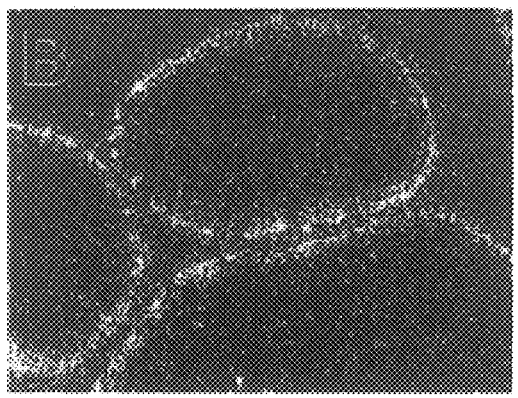
Figure 4E:
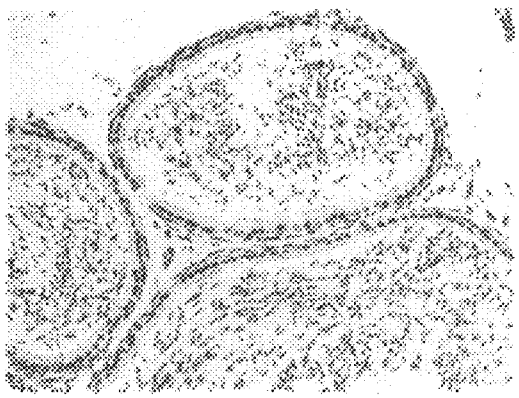
Figure 4C:
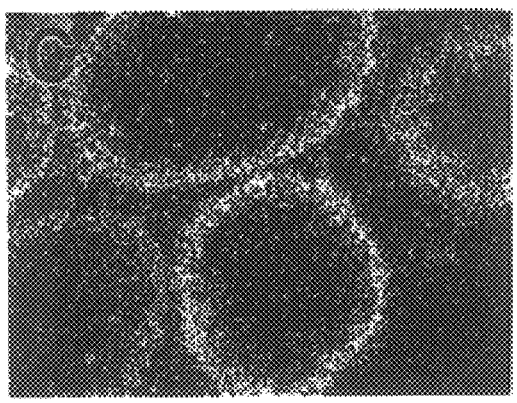
Figure 4F:
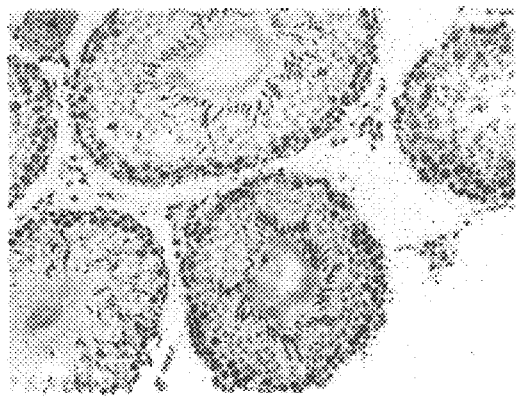
Figure 4D:
Figure 4G:
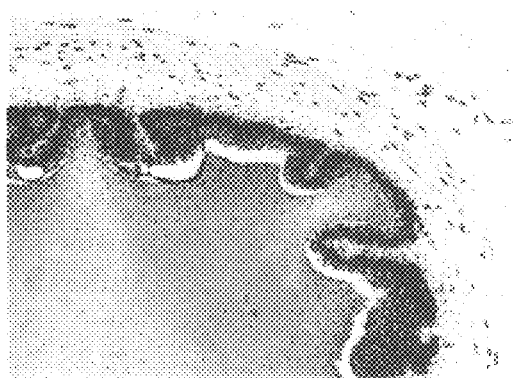

In addition to the polypeptides of FIGS. 2A–2C (SEQ ID NO: 4) and FIGS. 2A–2C and 3A–3D (SEQ ID NO: 6), also intended as part of this invention are fragments, precursors and derivatives thereof that are substantially biologically equivalent. By "substantially biologically equivalent" is meant having the same properties of the polypeptides as described herein, even if in lesser or greater degree. Preferably, such analogs will cross-react with antibodies raised against the polypeptides of FIGS. 2A–2C and 3A–3D. The term "derivative" is intended to mean molecules representing one or more amino acid substitutions, deletions and/or additions derived from the linear array of amino acids of such polypeptides, and which are also substantially biologically equivalent or share one or more biological properties.

Especially preferred derivatives in accordance with this invention are those which possess a degree of homology (i.e., identity of amino acid residues) with the proteins of FIGS. 2A–2C (SEQ ID NO: 4) or FIGS. 3A–3D (SEQ ID NO: 6) in excess of eighty percent (80%), and most preferably, in excess of ninety percent (90%), excluding the amino acid sequence of BPGF-1, above, which is outside the scope of the present invention.

Percent sequence identity can be determined by standard methods that are commonly used to compare the similarity in position of the amino acids of two polypeptides, to generate an optimal alignment of two respective sequences. By way of illustration, using a computer program such as BLAST or FASTA (FASTA is preferred for the present invention), two polypeptides are aligned for optimal matching of their respective amino acids (either along the full length of one or both sequences, or along a pre-determined portion of one or both sequences). The programs provide a "default" opening penalty and a "default" gap penalty, and a scoring matrix such as PAM 250. A standard scoring matrix can be used in conjunction with the computer program; see Dayhoff et al., in Atlas of Protein Sequence and Structure, Volume 5, Supplement 3 (1978). The percent identity (or "homology" as used herein) can then be calculated as follows:

$$\frac{\text{Total number of identical matches}}{[\text{No. of residues in region of alignment, not including non-identical residues at either or both ends and residues opposite a gap}]} \times 100$$

Polypeptides in accordance with this invention that are at least eighty percent (80%) identical, as determined by the above method, will typically have one or more amino acid substitutions, deletions, and/or insertions. Usually, the substitutions will be conservative so as to have little or no effect on the overall net charge, polarity, or hydrophobicity of the protein. Examples of conservative substitutions are set forth below.

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |

-continued

Conservative amino acid substitutions

| | |
|---|---|
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

PDPF polypeptides of this invention may or may not have an amino terminal methionine, depending on the manner in which they are prepared. Typically, an amino terminal methionine residue will be present when the polypeptide is produced recombinantly in a non-secreting bacterial (e.g., *E. coli*) strain as the host.

PDPF fragments included within this invention will be those that have less than the full length sequence, but which possess substantially the same biological activity and are truncated at the amino terminus, the carboxy terminus, and/or internally.

This invention also encompasses nucleic acid molecules encoding any of the above mentioned polypeptides. Besides the nucleic acid molecules having the nucleotide sequences shown in FIGS. 2A–2C (SEQ ID NO: 3) and FIGS. 3A–3D (SEQ ID NO: 5), also included are degenerate sequences thereof encoding the same polypeptides. In addition, this invention encompasses nucleic acid molecules encoding biologically active precursors, fragments and derivatives of the polypeptides described herein. In addition, the invention encompasses nucleic acid molecules encoding the complementary (i.e., antisense) strands, as well as DNA molecules which hybridize (or would hybridize but for the variability of nucleotide sequence due to the degeneracy of codons) to the DNA molecules of FIGS. 2A–2C and 3A–3D, to fragments or degenerate sequences thereof, or to their complementary strands, preferably under relatively stringent conditions (e.g., conditions such as described below). Excluded from this group is the nucleic acid molecule encoding BPGF-1. The present invention also embraces nucleic acid molecules that may encode additional amino acid residues flanking the 5' or 3' portions of the region encoding the "mature" PDPF polypeptide (i.e., the processed product harvested from the host), such as sequences encoding alternative pre/pro regions (i.e., sequences responsible for secretion of the polypeptide through cell membranes) in place of the "native" pre/pro regions. The additional sequences may also be noncoding sequences, including regulatory sequences such as promoters of transcription or translation, depending on the host cell. The nucleic acid molecules may even include various internal non-coding sequences (i.e., introns) known not to occur within genes.

As mentioned, the present invention contains within its scope DNA molecules which are hybridizable to complementary sequences under relatively stringent conditions. In general, as employed herein the term "stringent conditions" refers to hybridization and washing under conditions that permit the binding of a nucleic acid molecule such as an oligonucleotide or cDNA molecule to highly homologous sequences.

One stringent washing solution, suitable for use with cDNA probes at a temperature of 55–65° C., is composed of 0.015 M sodium chloride, 0.0015 M sodium citrate (0.1× SSC, where 1×SSC=0.15 M sodium chloride and 0.015 M sodium citrate) and 0.1 percent SDS. Another, slightly less stringent washing solution, is composed of 0.2×SSC and 0.1 percent SDS, and can be used at a temperature of between 50–65° C.

Where oligonucleotide probes are used to screen cDNA or genomic libraries, the following stringent washing conditions may be used. One protocol uses 6×SSC with 0.05 percent sodium pyrophosphate at a temperature of 35–62° C., depending on the length of the oligonucleotide probe. For example, 14-base pair probes are washed at 35–40° C., 17-base pair probes are washed at 45–50° C., 20-base pair probes are washed at 52–57° C., and 23-base pair probes are washed at 57–63° C. The temperature can be increased 2–6° C. where background non-specific binding appears to be high. Another protocol utilizes tetramethylammonium chloride (TMAC) for washing oligonucleotide probes. A suitable stringent washing solution is composed of 3 M TMAC, 50 mM Tris-HCl, pH 8.0, and 0.2 percent SDS. The washing temperature for use with this solution is a function of the length of the probe. For example, a 17-base pair probe is typically washed at about 45–50° C.

Also included within the scope of this invention are RNA molecules that are homologous to any of the aforementioned DNA molecules.

Recombinant Methods of Preparation

The full length polypeptides of the invention, or fragments or derivatives thereof, can be prepared using well known recombinant DNA technology methods such as those set forth in Sambrook et al., Molecular Cloning: A Laboratory Manual, Cold Spring Harbor Laboratory Press, Cold Spring Harbor, N.Y. (1989) and/or Ausubel et al., Editors, Current Protocols in Molecular Biology, Green Publishers Inc. and Wiley and Sons, New York (1994). A gene or cDNA encoding the polypeptide or truncated version thereof may be obtained, for example, by screening a genomic or cDNA library, or by PCR amplification. Alternatively, a gene encoding the polypeptide or fragment, or analog thereof, may be prepared by chemical synthesis using methods well known to the skilled artisan, such as those described by Engels et al. in Angew. Chem. Intl. Ed., Volume 28, pages 716–734 (1989). Typically, the DNA encoding the polypeptide will be several hundred nucleotides in length. Nucleic acids larger than about one hundred nucleotides can be synthesized as several fragments using these same methods and the fragments can then be ligated together to form a nucleotide sequence of the desired length.

The nucleic acid analogs may be produced using site directed mutagenesis or PCR amplification where the primer (s) have the desired point mutations (see Sambrook et al., above, and Ausubel et al., above, for descriptions of suitable mutagenesis techniques). Chemical synthesis using methods described by Engels et al., above, may also be used to prepare such variants. Preferred nucleic acid analogs are those containing nucleotide substitutions accounting for codon preference in the host cell to be used to produce the polypeptide. Other preferred variants are those encoding conservative amino acid changes (see above) as compared to wild type, and/or those designed to either generate or delete glycosylation and/or phosphorylation site(s) on the polypeptide.

The genes or cDNAs of this invention can be inserted into an appropriate expression vector for expression in a suitable host cell. The vector is selected to be functional in the particular host cell employed (i.e., the vector is compatible with the host cell machinery, such that amplification and/or expression of the gene can occur). The polypeptide, or fragment or derivative analog thereof, may be amplified/expressed in prokaryotic, yeast, insect (baculovirus systems) and/or eukaryotic host cells. Selection of the host cell will depend at least in part on whether the polypeptide expression product is to be glycosylated. If glycosylation is desired, then yeast, insect or mammalian host cells are preferred for use, in that yeast cells will glycosylate the polypeptide, and insect and mammalian cells can glycosylate and/or phosphorylate the polypeptide in a manner similar to "native" glycosylation and/or phosphorylation.

The vectors used in any of the host cells to express the polypeptide may also contain a 5' flanking sequence (also referred to as a "promoter") and other expression regulatory elements operatively linked to the DNA to be expressed, as well as enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below.

Optionally, the vector may also contain a "tag" sequence, i.e., an oligonucleotide sequence located at the 5' or 3' end of the polypeptide-coding sequence that encodes polyHis (such as hexaHis) or another small immunogenic sequence. This tag will be expressed along with the protein, and can serve as an affinity tag for purification of the polypeptide from the host cell. Optionally, the tag can subsequently be removed from the purified polypeptide by various means, for example, with use of a selective peptidase.

The 5' flanking sequence may be the native 5' flanking sequence, or it may be homologous (i.e., from the same species and/or strain as the host cell), heterologous (i.e., from a species other than the host cell species or strain), hybrid (i.e., a combination of 5' flanking sequences from more than one source), or synthetic. The source of the 5' flanking sequence may be any unicellular prokaryotic or eukaryotic organism, any vertebrate or invertebrate organism, or any plant, provided that the 5' flanking sequence is functional in, and can be activated by the host cell machinery.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, or by other methods known to the skilled artisan. Selection of suitable enzymes to accomplish this purpose will be readily apparent to one skilled in the art.

The origin of replication element is typically a part of prokaryotic expression vectors purchased commercially, and aids in the amplification of the vector in a host cell. Amplification of the vector to a certain copy number can, in some cases, be important for optimal expression of the polypeptide. If the vector of choice does not contain an origin of replication site, one may be chemically synthesized based on a known sequence, and then ligated into the vector.

The transcription termination element is typically located 3' to the end of the polypeptide coding sequence and serves to terminate transcription of the mRNA. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those referred to above.

A selectable marker gene element encodes a protein necessary for the survival and growth of a host cell grown in a selective culture medium. Typical selection marker genes encode proteins that: (a) confer resistance to antibiotics or other toxins, e.g., ampicillin, tetracycline or kanamycin for prokaryotic host cells, and, e.g., neomycin for mammalian host cells; (b) complement auxotrophic deficiencies of the cell; or (c) supply critical nutrients not available from complex media. Preferred selectable markers for use in prokaryotic expression are the kanamycin resistance gene, the ampicillin resistance gene, and the tetracycline resistance gene.

The ribosome binding element, commonly called the Shine-Dalgarno sequence (for prokaryotes) or the Kozak sequence (for eukaryotes), is necessary for the initiation of translation of mRNA. The element is typically located 3' to the promoter and 5' to the coding sequence of the polypeptide to be synthesized. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector. The Kozak sequence typically includes sequences immediately before and after the initiating codon. A preferred Kozak sequence is one that is associated with a high efficiency of initiation of translation at the AUG start codon.

In those cases where it is desirable for the polypeptide to be secreted from the host cell, a signal sequence may be used to direct the polypeptide out of the host cell where it is synthesized. Typically, the signal sequence is positioned in the coding region of nucleic acid sequence, or directly at the 5' end of the coding region. Many signal sequences have been identified, and any of them that are functional in the selected host cell may be used here. Consequently, the signal sequence may be homologous or heterologous to the polypeptide. Additionally, the signal sequence may be chemically synthesized using methods referred to above.

After the vector has been constructed and a nucleic acid has been inserted into the proper site of the vector, the completed vector may be inserted into a suitable host cell for amplification and/or polypeptide expression.

Host cells may be prokaryotic (such as *E. coli*) or eukaryotic (such as a yeast cell, an insect cell, or a vertebrate cell). The host cell, when cultured under appropriate conditions, can synthesize the polypeptide, which can subsequently be collected from the culture medium (if the host cell secretes it into the medium) or directly from the host cell producing it (if it is not secreted). After collection, the polypeptide can be purified using methods such as molecular sieve chromatography, affinity chromatography, and the like.

Selection of the host cell will depend in part on whether the polypeptide is to be glycosylated or phosphorylated (in this case eukaryotic host cells are preferred), and the manner in which the host cell is able to "fold" the polypeptide into its native tertiary structure (e.g., proper orientation of disulfide bridges, etc.) such that biologically active polypeptide is prepared by the cell. However, where the host cell does not synthesize biologically active polypeptide, it may be "folded" after synthesis using appropriate chemical conditions as discussed below.

Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. Other suitable mammalian cell lines are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Still other suitable mammalian cell lines include but are not limited to, HeLa, mouse L-929 cells, 3T3 lines derived from Swiss, Balb-c or NIH mice, BHK or HaK hamster cell lines.

Also useful as host cells are bacterial cells. For example, the various strains of E. coli (e.g., HB101, DH5a, DH10, and MC1061) are well-known as host cells in the field of biotechnology. Various strains of B. subtilis, Pseudomonas spp., other Bacillus spp., Streptomyces spp., and the like, may also be employed. Additionally, many strains of yeast cells known to those skilled in the art are also available as host cells for expression of the polypeptides of the present invention. Also, where desired, insect cells may be utilized as host cells. See, for example, Miller et al., Genetic Engineering, Volume 8, pages 277–298 (1986).

Insertion (also referred to as "transformation" or "transfection") of the vector into the selected host cell may be accomplished using such methods as calcium phosphate, electroporation, microinjection, lipofection or the DEAE-dextran method. The method selected will in part be a function of the type of host cell to be used. These methods and other suitable methods are well known to the skilled artisan, and are set forth, for example, in Sambrook et al., above.

The host cells containing the vector may be cultured using standard media well known to the skilled artisan. The media will usually contain all nutrients necessary for the growth and survival of the cells. Suitable media for culturing E. coli cells are, for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate and/or fetal calf serum, as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of polypeptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If the polypeptide has been designed to be secreted from the host cells, the majority of polypeptide will likely be found in the cell culture medium. If the polypeptide is not secreted, it will be present in the cytoplasm (for eukaryotic, gram-positive bacteria, and insect host cells) or in the periplasm (for gram-negative bacteria host cells).

For intracellular polypeptide, the host cells are typically first disrupted mechanically or osmotically to release the cytoplasmic contents into a buffered solution. The polypeptide is then isolated from this solution. Purification of the polypeptide from solution can thereafter be accomplished using a variety of techniques. If the polypeptide has been synthesized so that it contains a tag such as hexahistidine or other small peptide at either its carboxyl or amino terminus, it may essentially be purified in a one-step process by passing the solution through an affinity column where the column matrix has a high affinity for the tag or for the polypeptide directly (i.e., a monoclonal antibody). For example, polyhistidine binds with great affinity and specificity to nickel, thus an affinity column of nickel (such as the Qiagen nickel columns) can be used for purification. (See, for example, Ausubel et al., eds., Current Protocols in Molecular Biology, above).

Where, on the other hand, the polypeptide has no tag and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

If it is anticipated that the polypeptide will be found primarily in the periplasmic space of the bacteria or the cytoplasm of eukaryotic cells, the contents of the periplasm or cytoplasm, including inclusion bodies (e.g., gram-negative bacteria) if the processed polypeptide has formed such complexes, can be extracted from the host cell using any standard technique known to the skilled artisan. For example, the host cells can be lysed to release the contents of the periplasm by the use of a French press, homogenization, and/or sonication. The homogenate can then be centrifuged.

In addition to the use of recombinant DNA techniques, the polypeptides, fragments, and/or derivatives thereof, may be prepared by chemical synthesis methods (such as solid phase peptide synthesis) using methods known in the art, including those set forth by Merrifield et al. in the Journal of the American Chemical Society, Volume 85, page 2149 (1964), by Houghten et al. in the Proceedings of the National Academy of Science U.S.A., Volume 82, page 5132 (1985), and by Stewart and Young in Solid Phase Peptide Synthesis, Pierce Chemical Co, Rockford, Ill. (1984). Chemically synthesized polypeptides or fragments or analogs thereof may be oxidized using methods set forth in these references to form disulfide bridges. The resulting polypeptide products may be employed as biologically active or immunological substitutes for the natural, purified polypeptide.

Chemically modified polypeptide compositions where the polypeptide is linked to a polymer in order to modify properties are included within the scope of the present invention. The polymer is typically water soluble so that the protein to which it is attached does not precipitate in an aqueous environment, such as a physiological environment. The polymer may have a single reactive group, such as an active ester for acylation or an aldehyde for alkylation, so that the degree of polymerization may be controlled. A preferred reactive aldehyde is polyethylene glycol propionaldehyde, which is water stable, or mono C1–C10 alkoxy or aryloxy derivatives thereof (see U.S. Pat. No. 5,252,714). The polymer may be branched or unbranched. Preferably, for therapeutic use of the end-product preparation, the polymer will be pharmaceutically acceptable. The water soluble polymer, or mixture thereof if desired, may be selected from the group consisting of, for example, polyethylene glycol (PEG), monomethoxypolyethylene glycol, dextran, cellulose, or other carbohydrate based polymers, poly(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. The polymer preferred for chemical modification is polyethylene glycol.

Pegylation of the polypeptide (i.e., addition of polyethylene glycol chains) may be carried out by any of the pegylation reactions known in the art, as described for example in the following references: Focus on Growth Factors, Volume 3, Number 2, pages 4–10 (1992); EP 0 154 316; and EP 0 401 384. Preferably, the pegylation is carried out via an acylation reaction or an alkylation reaction with a reactive polyethylene glycol molecule (or an analogous reactive water-soluble polymer), in accordance with known methods.

The polypeptide growth factors of this invention (including fragments, derivatives and the above-described chemically modified products thereof) can be used alone or together with other components in tissue culture media to promote the growth and proliferation of responsive cells, e.g., prostate cells. Various assay methods can be used to detect and quantitatively measure such cell growth. Such methods include, merely by way of example, in vitro assays such as the uptake and elution of crystal violet dye; the incorporation of radioactive or non-radioactive labels, such as $^3$H-thymidine or bromodeoxy uridine, into precipitable cellular DNA, the bioreduction of MTS (Owen's reagent) to formazan by dehydrogenase enzymes in metabolically active cells, and the direct counting of cells following trypsinization and resuspension in media using a Coulter Counter.

Generation of Antibodies

The polypeptides of the invention, including fragments and/or derivatives thereof, may also be used to generate antibodies in accordance with standard methods. The antibodies may be polyclonal, monoclonal, recombinant, chimeric, single-chain and/or bispecific, etc. To improve the likelihood of producing an immune response, the amino acid sequence of the polypeptide can be analyzed to identify portions of the molecule that may be associated with increased immunogenicity. For example, the amino acid sequence may be subjected to computer analysis to identify surface epitopes, such as in accordance with the method of Hope and Woods, Proceedings of the National Academy of Science U.S.A., Volume 78, pages 3824–3828 (1981). Alternatively, the deduced amino acid sequence from different species can be compared and relatively non-homologous regions identified (e.g., sequences of at least about six contiguous amino acids in which at least about two amino acids differ from one species to the other). These non-homologous regions would be more likely to be immunogenic across various species.

Various procedures known in the art can be used for the production of polyclonal antibodies which recognize epitopes of the polypeptides of this invention. For the production of antibody, various host animals can be immunized by injection with the polypeptide, or fragment or derivative thereof, including but not limited to rabbits, mice, rats, etc. Various adjuvants may be used to increase the immunological response, depending on the host species, including but not limited to Freund's, mineral gels such as aluminum hydroxide (alum), surface active substances such as lysolecithin, pluronic polyols, polyanions, peptides, oil emulsions, keyhole limpet hemocyanins, dinitrophenol, and potentially useful human adjuvants such as Bacille Calmette-Guerin and *Corynebacterium parvum*.

For the preparation of monoclonal antibodies directed toward the polypeptides, any technique which provides for the production of antibody molecules by continuous cell lines in culture may be used. For example, the hybridoma technique originally developed by Kohler and Milstein which is described in Nature, Volume 256, pages 495–497 (1975), as well as the trioma technique, the human B-cell hybridoma technique described by Kozbor et al. in Immunology Today, Volume 4, page 72 (1983), and the EBV-hybridoma technique to produce monoclonal antibodies described by Cole et al. in "Monoclonal Antibodies and Cancer Therapy", Alan R. Liss, Inc., pages 77–96 (1985), are all useful for preparation of monoclonal antibodies in accordance with this invention.

In addition, molecular clones of an antibody to an epitope or epitopes of the polypeptides can be prepared with known techniques. In particular, recombinant DNA methodology may be used to construct nucleic acid sequences which encode a monoclonal antibody molecule or antigen-binding region thereof; see, for example, Maniatis et al., Molecular Cloning, A Laboratory Manual, Cold Spring Harbor Laboratory, Cold Spring Harbor, N.Y. (1982).

DESCRIPTION OF SPECIFIC EMBODIMENTS

The invention is now described in further detail with reference to the following specific test methods, procedures, and results.

Cloning of PDPF

From the cDNA sequence of BPGF-1 (SEQ ID NO: 1; See WO 96/04379), it could be seen that the predicted amino acid sequence (SEQ ID NO: 2) encoded by the long open reading frame of this nucleic acid sequence did not appear to have a signal sequence, as is usually found in a secreted protein. Consequently, an attempt was made to isolate other clones. More specifically, the nucleic acid sequence of SEQ ID NO: 1 was used to design polymerase chain reaction (PCR) primers to screen tissue cDNAs and also cDNA libraries for other BPGF clones. Initial screening of the first strand cDNAs indicated that BPGF is expressed in the human placenta. To prepare a cDNA library, cDNA was prepared from human placental polyA$^+$ RNA using a NotI-oligo(dT) primer and SalI adapter, then size-fractionated, and thereafter cloned into vector pSPORT1 (Bethesda Research Laboratories, Bethesda, Md.), using the procedures provided by the manufacturer; see D'Alessio et al., Focus, Volume 12, pages 47–48 (1990). Transformants were divided into fifty-two pools of approximately six thousand clones each, and plasmid DNA (0.5 mg/L) was prepared from each pool; Del Sal et al., Biotechniques, Volume 7, pages 514–520 (1989). The pooled DNAs were mixed four at a time into thirteen master pools of approximately twenty thousand clones each. Approximately 100–200 ng of each master pool DNA was used as template in a PCR procedure carried out with the primers

5'TGGAGTTCTTCGCCTCCTGGT (SEQ ID NO: 8)

and

5'TGGTGAGCCCAGAGAGTCTCTG (SEQ ID NO: 9).

The four individual pools from each of the positive master pools were then screened by PCR using the same two primers, and positives were verified by PCR with use of primers

5'TGGAGTTCTTCGCCTCCTGGT (SEQ ID NO: 8)

and

5'ATGATGGGACTCCACGGCGTCAAT (SEQ ID NO: 10).

One of the positive pools was plated, and colony lifts on nitrocellulose filters were hybridized overnight in a hybridization solution (0.9M NaCl, 0.09M sodium citrate, 1% w/v Ficoll type 400, 1% w/v Polyvinylpyrrolidone, 1% w/v BSA, and 0.1% w/v SDS) at a temperature of 54° C., with $^{32}$P-labeled 5'GGGAAGCCAGGGATGTTGAAGTCT (SEQ ID NO: 11). Filters were washed with a washing solution (0.3M NaCl, 0.03M sodium citrate and 0.5% SDS), at room temperature for one hour, followed by a fifteen-minute wash at 54° C., to remove unhybridized probe. Filters were exposed to film overnight.

The following day, individual positive colonies were picked and screened by PCR using as primers

5'CGAAGAGTACCTGGCTCTGATC (SEQ ID NO: 12)

and

5'TGGTGAGCCCAGAGAGTCTCTG (SEQ ID NO: 9).

The colonies were also screened with

5'GGGAAGCCAGGGATGTTGAAGTCT (SEQ ID NO: 11), and

5'TGGAGTTCTTCGCCTCCTGGT (SEQ ID NO: 8).

Plasmid DNA from the positive clones was sequenced. Two cDNA clones were isolated. The sequence of one of the clones included an open reading frame consisting of 1812 bases having the nucleic acid sequence shown in FIGS. 2A–2C (SEQ ID NO: 3), which encodes a protein of 604 amino acids, also shown in FIGS. 2A–2C (SEQ ID NO: 4), beginning with what is most likely a signal peptide. The second clone contained a large region of sequence identity with the first clone, the 5' end of the second clone aligning with nucleotide 429 of the first clone. It is likely that the second clone was the result of 5'-end truncation that occurred in the process of cloning. The predicted open reading frame obtained by appending the sequence of clone 2 to nucleotides 1–428 of the open reading frame of clone 1 results in a molecule of 2103 nucleotides in length, shown in FIGS. 3A–3D (SEQ ID NO: 5). This DNA sequence encodes a protein of 701 amino acids in length, the predicted amino acid sequence of which (SEQ ID NO: 6) is also shown in FIGS. 3A–3D.

Recombinant Expression of PDPFs

"293" cells (American Type Culture Collection, Rockville, Md., accession no. CRL 1573), which are human embryonic kidney cells transfected with the Ad5 adenovirus strain, were transfected with the large T antigen of SV40 to give a cell line designated as "293T". These cells were plated in a fibronectin-coated six-well plate at $1 \times 10^6$ cells/well. The cells were then incubated overnight at a temperature of 37° C., under an atmosphere of 5% $CO_2$. Water and 5 µg of PDPF/pJT2 plasmid DNA ($H_2O$+DNA=90 µl) were combined, then 100 µl of 2× Hepes buffered saline were added to this mixture. The PDPF/pJT2 vector was constructed by subcloning the cDNA for PDPF-1 or PDPF-2 polypeptide into expression vector pJT2 (pJT2 is a known vector described in published PCT application WO 94/28133). The resulting mixture was sterile filtered with a Costar spin-x filter. Then, 10 µl of 2.5 M $CaCl_2$ were added and mixed, and the mixture was permitted to stand at room temperature under a hood for thirty minutes. Air was bubbled into each DNA mixture (2 ml pipette+20 µl tip). One milliliter of media was removed from a well and combined with the DNA mixture, then transferred to the 293T cells and the cells were incubated overnight at 37° C., under 5% $CO_2$. The media were separated from the cells by aspiration and replaced with 2.5 ml of Iscove's Modified Dulbecco's Medium per well. The cells were incubated for three to four days at 37° C., under 5% $CO_2$. The conditioned media were harvested and the cellular debris was pelleted.

In Situ Hybridization Analysis of PDPF

These studies were performed for the detection of the presence of mRNA in various rat tissues of PDPF. For this analysis, a probe of about one kilobase prepared against the N-terminus of mouse PDPF was used. A panel of normal embryonic and adult rat tissues was fixed in 4% paraformaldehyde, embedded in paraffin, and sectioned at 5 µm. Prior to in situ hybridization, tissues were permeabilized with 0.2M HCL, followed by digestion with Proteinase K and acetylation with triethanolamine and acetic anhydride. Sections were hybridized with a $^{33}$P-labeled riboprobe overnight at 55° C., then subjected to a high stringency wash in 0.1× SSC at 60° C. Slides were dipped in Kodak NTB2 emulsion, exposed at 4° C. for two to three weeks, developed, and then counterstained. Sections were examined with darkfield and standard illumination to allow simultaneous evaluation of tissue morphology and hybridization signal. The results are shown in FIGS. 4A–4G.

Overall, the N-terminal probe produced a relatively restricted distribution of signal in the tissue sections from both embryo and adult rat, with little or no background signal. A majority of the signal in positive tissues was localized to ductal, squamous or columnar epithelium. In embryonic tissue, strong signal (indicative of the presence of significant amounts of mRNA for PDPF) was observed in the pancreas, the kidney collecting tubules, at the nasal-tracheal-esophageal junction, the heart, skin, and in the placenta. A strong signal was also observed in several large vessels such as the hepatic and pulmonary arteries and in the endocardium of the heart, but it appeared to be absent from the microvasculature. Moderate or diffuse signal was detected in adrenal medullary cells, the intestine, ovary and testes. The brain, lungs, thymus, skeletal muscle and liver were negative. Some scattered cells of unknown origin were observed in developing bones, ribs, vertebrae and around jaw cartilage. In adult rat tissue, expression of mRNA for PDPF was strong in several organs. In the male reproductive system, there was intense signal in the epithelium of the testes and in the vesicular gland. There was also strong signal in the epididymus and prostate gland, and variable signal in the seminiferous tubules within the testis. Some developing spermatids also expressed some signal. There was also signal in the female reproductive system, including the germinal epithelium of growing and primordial follicles, but not in the corpus luteum of the ovaries, and some signal in the outermost layer of the stratified epithelium of the uterus. Breast ductal epithelium had intense signal. The stomach had a high level of signal in keratinized and glandular epithelium, as did the epithelial keratinocytes of the esophagus and the skin. In the skin, the signal for PDPF was particularly intense in the cells adjacent to the hair shaft (these cells are probably sebaceous cells). The strong signal observed in embryonic pancreas was found to have decreased in the adult to a level that was only modestly above background. In the adult intestine, there was a variable level of signal in the epithelium that was strongest in the colon. In the lung, there was modest signal around some large bronchi, and also some signal around some ducts in the submaxillary gland. Other tissues did not have strong specific signal, although several did have a grain density above background.

Human tumors from various sources were also screened with the PDPF probe. Very strong signal was observed in two different breast and lung tumors that were sampled from metastatic sites in the brain. Another metastatic breast tumor also expressed a moderate signal for PDPF mRNA.

Figure 5:
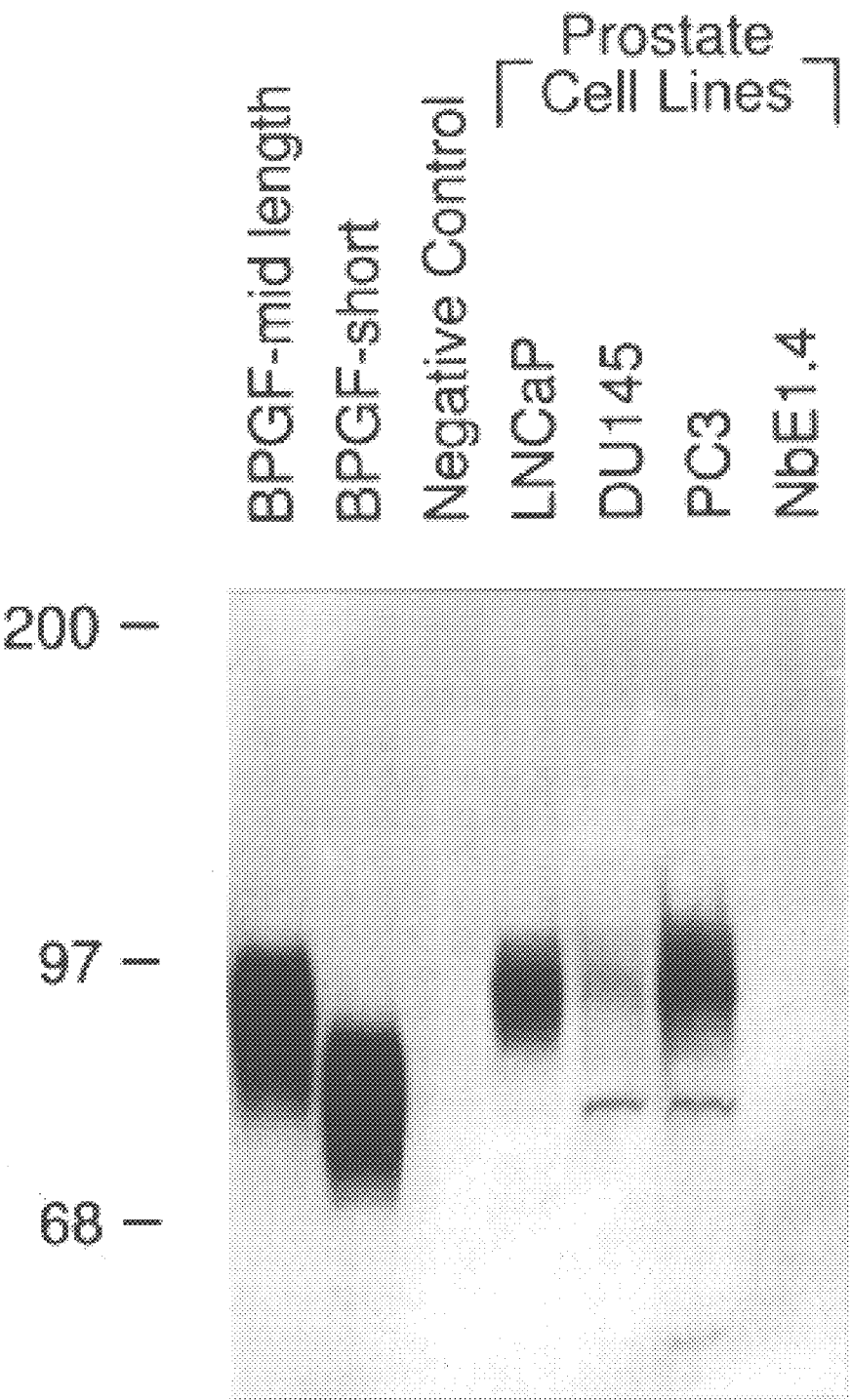
FIG. 5. This figure shows the expression of PDPF in prostate carcinoma cells and normal prostate epithelial cells. Conditioned media (CM) was collected and assayed by Western blot using a PDPF-specific antibody. Lane 1, recombinant form of protein PDPF-1 (SEQ ID NO: 4). Lane 2, recombinant form of protein PDPF-2 (SEQ ID NO: 6). Lane 3, CM from untransfected cells. Lane 4, CM from LNCaP prostate carcinoma cells. Lane 5, CM from DU145 prostate carcinoma cells. Lane 6, CM from PC3 prostate carcinoma cells. Lane 7, CM from NbE1.4 normal prostate epithelial cells.

The expression of PDPF at the protein level was also examined in several prostate carcinoma cell lines and in normal prostate epithelial cells. Results are shown in FIG. 5. These proteins were detected in the conditioned media of all three prostate carcinoma cell lines tested, but not in normal prostate epithelial cells. The longer form (SEQ ID NO: 6) was expressed strongly in LNCaP and PC3 carcinoma cells, and weakly in DU145 cells. In contrast, the shorter form (SEQ ID NO: 4) was expressed in DU145 and PC3 carcinoma cells at a much lower level, and not at all in LNCaP cells. These data support the in vitro data (see below) suggesting that these proteins are associated with, and active on, prostate carcinoma cells. In addition, these results suggest that the proteins may function as autocrine growth factors in prostate carcinoma cells. Expression was also analyzed in bone stromal tumor cell lines. Strong immunoreactive bands, corresponding to both the longer and shorter forms, were detected in the conditioned media of OHS4 and U20S osteosarcoma cells. Expression in two other osteosarcoma cell lines, SaOs2 and TE85, was at a much lower level, and no expression could be detected in MG63 osteosarcoma cells. These data confirm that osteosarcoma cells, which are cells derived from the bone stroma, express and secrete PDPF.

Procedure for Cell Proliferation Assays

Cells were plated at 2–5×10³ cells/well into 96-well plates in 100 ml of DMEM (GIBCO/BRL, Gaithersburg, Md.) or RPMI (GIBCO/BRL, Gaithersburg, Md.) containing 5% charcoal/dextran-stripped fetal bovine serum (Gemini Bio-Products, Calabasas, Calif.), L-glutamine, non-essential amino acids and penicillin/streptomycin. The cell cultures were allowed to attach and spread overnight. On the following day, the media was aspirated and replaced by the assay media, DMEM or RPMI containing 2–5% charcoal/dextran-stripped fetal bovine serum, L-glutamine, non-essential amino acids and penicillin/streptomycin, and the samples to be tested. Test samples consisted of 1× or 5× concentrated conditioned media (CM) from 293T cells that had been separately transfected with DNA for PDPF-1 or PDPF-2 (see above). Western blots demonstrated that the transfected 293T cell-conditioned media contained significant levels of PDPF at the expected molecular weight for each isoform. As a negative control, 293T cells were mock transfected (i.e., with non-PDPF containing vector), after which conditioned media were collected and tested in parallel. Western blots of negative control conditioned media showed no expression of any PDPF. Conditioned media from PDPF or mock-transfected 293T cells were added to triplicate wells for each data point. Additional controls included cells incubated with assay media or growth media alone. Plates were incubated for 3–4 days before cell proliferation was determined using the Celltiter 96 Aqueous non-radioactive cell proliferation assay (Promega, Madison, Wis.), and read on a Molecular Devices UVmax kinetic microplate reader at 490 nm. Results for each data point were expressed as the mean from triplicate wells±standard deviation. PDPF was deemed to stimulate proliferation of a cell line if an increase of at least 20% over negative controls was observed.

Results of Cell Proliferation Assay

PDPF-1 (SEQ ID NO: 4), i.e., the "shorter" PDPF form, and PDPF-2 (SEQ ID NO: 6), i.e., the "longer" PDPF form, were evaluated for mitogenic activity against various normal and abnormal (cancer) cell lines. The results of this evaluation are presented in Table 1 below. Designations for the cell lines tested are as follows: NbE 1.4 (normal rat prostate epithelial cells); LNCaP (human prostate carcinoma cells-lymph node metastasis); IEC 18 (normal rat ileum epithelial cells, i.e., small intestine); HUVEC (human umbilical vein endothelial cells); SaOS2 (human primary osteogenic sarcoma cells); HEPM (human embryonal palatal mesenchyme cells); MiaPaCa (human pancreatic carcinoma cells); JAR (human placental choriocarcinoma cells); PC-3 (human prostate adenocarcinoma cells-bony metastasis); DU145 (human prostate carcinoma cells-brain metastasis); Rat2 (normal rat embryonic fibroblasts); FADU (human pharynx squamous cell carcinoma cells); CAPAN I (human pancreatic adenocarcinoma cells—liver metastasis); CAPAN II (human pancreatic adenocarcinoma cells); and SW 480 (human colon adenocarcinoma cells). As indicated above, proliferation was considered to have occurred if there was an increase in cell population of at least twenty percent over the negative controls. Within this criterion, the symbol "++" indicates strong proliferation, "+" indicates moderate proliferation, "--" indicates no proliferation, and "±" indicates marginal proliferation. "N.D." indicates value was not determined.

TABLE 1

| | Cell Proliferation Assay | | |
| --- | --- | --- | --- |
| | 1× CM | | 5× CM |
| Cell Line | PDPF-1 SEQ. ID NO: 4 | PDPF-2 SEQ. ID NO: 6 | PDPF-1 SEQ ID NO: 4 |
| NbE 1.4 | -- | -- | -- |
| LNCaP | ++ | +/- | + |
| IEC 18 | +/- | N.D. | +/- |
| HUVEC | ++ | N.D. | ++ |
| SaOS2 | + | -- | -- |
| HEPM | + | -- | -- |
| MiaPaCa | -- | -- | -- |
| JAR | ++ | ++ | +/- |
| PC-3 | -- | -- | -- |
| DU145 | + | + | -- |
| Rat2 | -- | N.D. | -- |
| FADU | ++ | -- | -- |
| CAPAN I | -- | N.D. | -- |
| CAPAN II | -- | N.D. | -- |
| SW 480 | -- | N.D. | -- |

Useful Applications

Based on the foregoing results, it is expected that the PDPF proteins of this invention will be useful as growth factors to promote the proliferation, growth and survival of responsive cells tissues, including but not necessarily limited to prostate and epithelial cells. Because of the demonstrated effect of PDPF on prostate cancer cells in vitro (above), this growth factor should prove especially useful in research studies for the improved understanding of the development and progression of prostate cancer. For in vivo applications, the polypeptides of this invention can be formulated into pharmaceutically acceptable compositions comprising an effective cell or tissue growth promoting amount of the polypeptide and a pharmaceutically inert carrier, excipient and/or diluent, optionally together with other conventional ingredients.

The polypeptide growth factors of this invention are also expected to be utilizable in the identification and development of inhibitors of PDPF-mediated tumor growth, as in vitro assays and test methods designed to detect any appreciable mediation of cell proliferation, growth or survival activity of the factors in the presence of other specific molecules. Such inhibitors or "antagonists" of PDPF can serve as anti-tumor agents for the treatment of PDPF-stimulated tumor growth.

Antibodies specific to PDPF and nucleic acids such as DNA encoding full length or partial sequences of PDPF, as described herein, will be useful in the diagnosis and treatment of diseases involving prostate or epithelial tumors. The antibodies of this invention can be used therapeutically, such as to inhibit binding of the polypeptide to its receptor. The antibodies can further be used for diagnostic purposes, such as in labeled form to detect the presence of the polypeptide in a body fluid, tissue sample or other extract. In one method, a biological sample comprising a tissue or fluid specimen is contacted with a labeled (radioactively or fluorescently) antibody specific to PDPF, and the labeled reaction product of the antibody and PDPF is detected. In another method, a tissue or fluid specimen is contacted with a labeled probe for a nucleic acid molecule that encodes PDPF, and the labeled hybridization product is detected.

Deposits of Microorganisms

The following recombinant plasmid DNA were deposited on Oct. 4, 1996, with the American Type Culture Collection, 10801 University Boulevard, Manassas, Va. 20110-2209. The first listed contains cDNA encoding PDPF-1 (see nucleotide SEQ ID NO: 3), and the second (SEQ ID NO: 7).

| Deposit Name | ATTC Accession No. |
| --- | --- |
| pSPORT1: PDPF-1 p2N14.4 | 98194 |
| pGEM5: PDPF-2 cl.1 | 98195 |

What is claimed is:

1. A method for promoting the growth and proliferation of cells comprising contacting such cells which are responsive thereto with an effective amount of a placental-derived prostate growth factor having an amino acid sequence selected from the group consisting of SEQ ID NO: 4 and SEQ ID NO: 6.

2. A method according to claim 1 in which the cells are prostate cells.

3. A method according to claim 1 in which the cells are epithelial cells.

4. A method according to claim 1 which is carried out in vitro.

5. A method according to claim 1 which is carried out in vivo.

* * * * *

UNITED STATES PATENT AND TRADEMARK OFFICE
CERTIFICATE OF CORRECTION

PATENT NO. : 6,075,008
DATED : June 13, 2000
INVENTOR(S) : Farrell, et al.

It is certified that error appears in the above-identified patent and that said Letters Patent is hereby corrected as shown below:

Column 3, line 66: Remove the phrase "and FIGS. 2A-2C".

Column 18, line 16: Insert after "second" and before "(SEQ ID NO: 7)"
-- listed contains cDNA encoding PDPF-2 --.

Signed and Sealed this

Twenty-second Day of May, 2001

*Attest:*

NICHOLAS P. GODICI

*Attesting Officer*   *Acting Director of the United States Patent and Trademark Office*

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 1617 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
ATGGAATCCA GGTCCTTCTA TACCGCTTAC CTGCAGAGAC TCTCTGGGCT CACCAGGGAG      60

GCTGCCCAGA CCACAGTTGC ACCAACCACT GCTAACAAGA TAGCTCCCAC TGTTTGGAAA     120

TTGGCAGATC GCTCCAAGAT CTACATGGCT GACCTGGAAT CTGCACTGCA CTACATCCTG     180

CGGATAGAAG TGGGCAGGTT CCCGGTCCTG GAAGGGCAGC GCCTGGGTGG CCCTGAAAAA     240

GTTTGTGGCA GTTCTGGCCA AGTATTTCCT GGGCGGCCCT TAGTCCAGAA CTTTCTGCAC     300

TCCGTGAATG AATGGCTCAA GAGGCAGAAG AGAAATAAAA TTCCCTACAG TTTCTTTAAA     360

ACTGCCCTGG ACGACAGGAA AGAGGGTGCC GTTCTTGCCA AGAAGGTGAA CTGGATTGGC     420

TGCCAGGGGA GTGAGCCGCA TTTCCGGGGC TTTCCCTGCT CCTGTGGGTC CTCTTCCACT     480

TCTAGACTGT GCAGGCAGCT CGGATCAAAA TGTAGACCAC TCACAGGAAG CACGCAAGGC     540

CAAGGAGGTC CTCCCAGCCA TCCGAGGCTA GCTGCACTAC TTCTTCGGCT GCCGAGACTG     600

CGCAAGCCAC TTCGAGCAGA TGCTGCTGCC TCCATGCACC GGGTGGGGAG TCCCAACGCC     660

GCTGTCCTCT GGCTCTGGTC TAGCCACAAC AGGGTCAATG CTCGCTTGCA GGTGCCCCCA     720

GCGAGGACCC CCAGTTCCCC AAGGTGCAGT GGCCACCCCG TGAACTTTGT TCTGCCTGCC     780

ACAATGAACG CCTGGATGTG CCCGTGTGGG ACGTGGAAGC CACCCTCAAC TTCCTCAAGG     840

CCCACTTCTC CCCAAGCAAC ATCATCCTGG ACTTCCCTGC AGCTGGGTCA GCTGCCGGAG     900
```

```
GGATGTGCAG AATGTGCAGC CGCCCCAGAG CTGGCGATGG GAGCCCTGGA GCTGGAAAGC      960

CGGAATTCAA CTCTGGACCC TGGGAAGCCT GAGATGATGA AGTCCCCCAC AAACACCACC     1020

CCACATGTGC CGGCTGAGGG ACCTGAGGCA AGTCGACCCC CGAAGCTGCA CCCTGGCCTC     1080

AGAGCTGCAC CAGGCCAGGA GCCTCCTGAG CACATGGCAG ACGTTCAGAG GAATGAGCAG     1140

GACGAGCCGC TTGGGCAGTG GCACTTACGA AGCGAGACAC AGGGGCTGCA TTGCTGGCTG     1200

AGTCCAGGGC TGAGAAGAAC CGCCTCTGGG GCCCTTTGGA GGTCAGGCGC GTGGGCCGCA     1260

GCTCCAAGCA GCTGGTCGAC ATCCCTGAGG CCAGCTGGAG GCCCGAGCTG GACGGGCCGA     1320

GGCCAGTGGC TGCAGGTGCT GGGAGGGGGC TTCTCTTACC TGGACATCAG CCTCTGTGTG     1380

GGGCTCTATC CCTGTCCTTC ATGGGCCTGC TGGCATGTAC ACCTACTTCC AGGCCAAGAT     1440

AAGGCCCTGA ACCGGATGCT GGCCACCCTG CAGCCTGAAC CACCTGGGGA GGAGGCGGGA     1500

GAGGGAGCTG CCATCTCTAG GCACCTCAAG CCCCCTGACC CCATTCCCTC CCCTCCCACC     1560

CCTTGCTCCT TGTCTGGCCT AGAAGTGTGG GAAATTCAGG AAAACGAGTT GCTCCAG       1617

(2) INFORMATION FOR SEQ ID NO:2:

(i) SEQUENCE CHARACTERISTICS:
        (A) LENGTH: 539 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Glu Ser Arg Ser Phe Tyr Thr Ala Tyr Leu Gln Arg Leu Ser Gly
1               5                  10                  15

Leu Thr Arg Glu Ala Ala Gln Thr Thr Val Ala Pro Thr Thr Ala Asn
            20                  25                  30

Lys Ile Ala Pro Thr Val Trp Lys Leu Ala Asp Arg Ser Lys Ile Tyr
        35                  40                  45

Met Ala Asp Leu Glu Ser Ala Leu His Tyr Ile Leu Arg Ile Glu Val
    50                  55                  60

Gly Arg Phe Pro Val Leu Glu Gly Gln Arg Leu Gly Gly Pro Glu Lys
65                  70                  75                  80

Val Cys Gly Ser Ser Gln Val Phe Pro Gly Arg Pro Leu Val Gln
                85                  90                  95

Asn Phe Leu His Ser Val Asn Glu Trp Leu Lys Arg Gln Lys Arg Asn
                100                 105                 110

Lys Ile Pro Tyr Ser Phe Phe Lys Thr Ala Leu Asp Asp Arg Lys Glu
            115                 120                 125

Gly Ala Val Leu Ala Lys Lys Val Asn Trp Ile Gly Cys Gln Gly Ser
        130                 135                 140

Glu Pro His Phe Arg Gly Phe Pro Cys Ser Cys Gly Ser Ser Ser Thr
145                 150                 155                 160

Ser Arg Leu Cys Arg Gln Leu Gly Ser Lys Cys Arg Pro Leu Thr Gly
                165                 170                 175

Ser Thr Gln Gly Gln Gly Gly Pro Pro Ser His Pro Arg Leu Ala Ala
            180                 185                 190

Leu Leu Leu Arg Leu Pro Arg Leu Arg Lys Pro Leu Arg Ala Asp Ala
        195                 200                 205

Ala Ala Ser Met His Arg Val Gly Ser Pro Asn Ala Ala Val Leu Trp
    210                 215                 220
```

-continued

```
Leu Trp Ser Ser His Asn Arg Val Asn Ala Arg Leu Gln Val Pro Pro
225                 230                 235                 240

Ala Arg Thr Pro Ser Ser Pro Arg Cys Ser Gly His Pro Val Asn Phe
            245                 250                 255

Val Leu Pro Ala Thr Met Asn Ala Trp Met Cys Pro Cys Gly Thr Trp
        260                 265                 270

Lys Pro Pro Ser Thr Ser Ser Arg Pro Thr Ser Pro Gln Ala Thr Ser
    275                 280                 285

Ser Trp Thr Ser Leu Gln Leu Gly Gln Leu Pro Glu Gly Cys Ala Glu
290                 295                 300

Cys Ala Ala Ala Pro Glu Leu Ala Met Gly Ala Leu Glu Leu Glu Ser
305                 310                 315                 320

Arg Asn Ser Thr Leu Asp Pro Gly Lys Pro Glu Met Met Lys Ser Pro
                325                 330                 335

Thr Asn Thr Thr Pro His Val Pro Ala Glu Gly Pro Glu Ala Ser Arg
                340                 345                 350

Pro Pro Lys Leu His Pro Gly Leu Arg Ala Ala Pro Gly Gln Glu Pro
            355                 360                 365

Pro Glu His Met Ala Asp Val Gln Arg Asn Glu Gln Asp Glu Pro Leu
    370                 375                 380

Gly Gln Trp His Leu Arg Ser Glu Thr Gln Gly Leu His Cys Trp Leu
385                 390                 395                 400

Ser Pro Gly Leu Arg Arg Thr Ala Ser Gly Ala Leu Trp Arg Ser Gly
                405                 410                 415

Ala Trp Ala Ala Ala Pro Ser Ser Trp Ser Thr Ser Leu Arg Pro Ala
                420                 425                 430

Gly Gly Pro Ser Trp Thr Gly Arg Gly Gln Trp Leu Gln Val Leu Gly
            435                 440                 445

Gly Gly Phe Ser Tyr Leu Asp Ile Ser Leu Cys Val Gly Leu Tyr Pro
        450                 455                 460

Cys Pro Ser Trp Ala Cys Trp His Val His Leu Leu Pro Gly Gln Asp
465                 470                 475                 480

Lys Ala Leu Asn Arg Met Leu Ala Thr Leu Gln Pro Glu Pro Pro Gly
                485                 490                 495

Glu Glu Ala Gly Glu Gly Ala Ala Ile Ser Arg His Leu Lys Pro Pro
            500                 505                 510

Asp Pro Ile Pro Ser Pro Pro Thr Pro Cys Ser Leu Ser Gly Leu Glu
        515                 520                 525

Val Trp Glu Ile Gln Glu Asn Glu Leu Leu Gln
530                 535
```

(2) INFORMATION FOR SEQ ID NO:3:

(i) SEQUENCE CHARACTERISTICS:
        (A) LENGTH: 1812 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
ATGAGGAGGT GCAACAGCGG CTCCGGGCCG CCGCCGTCGC TGCTGCTGCT GCTGCTGTGG      60

CTGCTCGCGG TTCCCGGCGC TAACGCGGCC CCGCGGTCGG CGCTCTATTC GCCTTCCGAC     120

CCGCTGACGC TGCTGCAGGC GGACACGGTG CGCGGCGCGG TGCTGGGCTC CCGCAGCGCC     180
```

-continued

```
TGGGCCGTGG AGTTCTTCGC CTCCTGGTGC GGCCACTGCA TCGCCTTCGC CCCGACGTGG    240

AAGGCGCTGG CCGAAGACGT CAAAGCCTGG AGGCCGGCCC TGTATCTCGC CGCCCTGGAC    300

TGTGCTGAGG AGACCAACAG TGCAGTCTGC AGAGACTTCA ACATCCCTGG CTTCCCGACT    360

GTGAGGTTCT TCAAGGCCTT TACCAAGAAC GGCTCGGGAG CAGTATTTCC AGTGGCTGGT    420

GCTGACGTGC AGACGCTGCG GGAGAGGCTC ATTGACGCCC TGGAGTCCCA TCATGACACG    480

TGGCCCCCAG CCTGTCCCCC ACTGGAGCCT GCCAAGCTGG AGGAGATTGA TGGATTCTTT    540

GCGAGAAATA ACGAAGAGTA CCTGGCTCTG ATCTTTGAAA AGGGAGGCTC CTACCTGGGT    600

AGAGAGGTGG CTCTGGACCT GTCCCAGCAC AAAGGCGTGG CGGTGCGCAG GGTGCTGAAC    660

ACAGAGGCCA ATGGTGTGAG AAAGTTTGGT GTCACCGACT TCCCCTCTTG CTACCTGCTG    720

TTCCGGAATG GCTCTGTCTC CCGAGTCCCC GTGCTCATGG AATCCAGGTC CTTCTATACC    780

GCTTACCTGC AGAGACTCTC TGGGCTCACC AGGGAGGCTG CCCAGACCAC AGTTGCACCA    840

ACCACTGCTA ACAAGATAGC TCCCACTGTT TGGAAATTGG CAGATCGCTC CAAGATCTAC    900

ATGGCTGACC TGGAATCTGC ACTGCACTAC ATCCTGCGGA TAGAAGTGGG CAGGTTCCCG    960

GTCCTGGAAG GCAGCGCCT GGTGGCCCTG AAAAAGTTTG TGGCAGTGCT GGCCAAGTAT    1020

TTCCCTGGCC GGCCCTTAGT CCAGAACTTC CTGCACTCCG TGAATGAATG CTCAAGAGG    1080

CAGAAGAGAA ATAAAATTCC CTACAGTTTC TTTAAAACTG CCCTGGACGA CAGGAAAGAG    1140

GGTGCCGTTC TTGCCAAGAA GGTGAACTGG ATTGGCTGCC AGGGGAGTGA GCCGCATTTC    1200

CGGGGCTTTC CCTGCTCCCT GTGGGTCCTC TTCCACTTCT TGACTGTGCA GGCAGCTCGC    1260

CAAAATGTAG ACCACTCACA GGAAGCAGCC AAGGCCAAGG AGGTCCTCCC AGCCATCCGA    1320

GGCTACGTGC ACTACTTCTT CGGCTGCCGA GACTGCGCTA GCCACTTCGA GCAGATGGCT    1380

GCTGCCTCCA TGCACCGGGT GGGGAGTCCC AACGCCGCTG TCCTCTGGCT CTGGTCTAGC    1440

CACAACAGGG TCAATGCTCG CCTTGCAGGT GCCCCCAGCG AGGACCCCCA GTTCCCCAAG    1500

GTGCAGTGGC CACCCGTGA ACTTTGTTCT GCCTGCCACA ATGAACGCCT GGATGTGCCC    1560

GTGTGGGACG TGGAAGCCAC CCTCAACTTC CTCAAGGCCC ACTTCTCCCC AAGCAACATC    1620

ATCCTGGACT TCCCTGCAGC TGGGTCAGCT GCCCGGAGGG ATGTGCAGAA TGTGGCAGCC    1680

GCCCCAGAGC TGGCGATGGG AGCCCTGGAG CTGGAAAGCC GGAATTCAAC TCTGGACCCT    1740

GGGAAGCCTG AGATGATGAA GTCCCCCACA AACACCACCC CACATGTGCC GGCTGAGGGA    1800

CCTGAGCTTA TT                                                        1812
```

(2) INFORMATION FOR SEQ ID NO:4:

(i) SEQUENCE CHARACTERISTICS:
    (A) LENGTH: 604 amino acids
    (B) TYPE: amino acid
    (C) STRANDEDNESS: single
    (D) TOPOLOGY: linear (ii) MOLECULE TYPE: protein (ix) FEATURE:
    (A) NAME/KEY: CDS
    (B) LOCATION: 1..1812

(xi) SEQUENCE DESCRIPTION: SEQ ID NO:4:

```
Met Arg Arg Cys Asn Ser Gly Ser Gly Pro Pro Ser Leu Leu Leu
 1               5                  10                  15

Leu Leu Leu Trp Leu Leu Ala Val Pro Gly Ala Asn Ala Ala Pro Arg
            20                  25                  30
```

```
-continued

Ser Ala Leu Tyr Ser Pro Ser Asp Pro Leu Thr Leu Gln Ala Asp
        35                  40                  45

Thr Val Arg Gly Ala Val Leu Gly Ser Arg Ser Ala Trp Ala Val Glu
 50                  55                  60

Phe Phe Ala Ser Trp Cys Gly His Cys Ile Ala Phe Ala Pro Thr Trp
 65                  70                  75                  80

Lys Ala Leu Ala Glu Asp Val Lys Ala Trp Arg Pro Ala Leu Tyr Leu
                 85                  90                  95

Ala Ala Leu Asp Cys Ala Glu Glu Thr Asn Ser Ala Val Cys Arg Asp
                100                 105                 110

Phe Asn Ile Pro Gly Phe Pro Thr Val Arg Phe Phe Lys Ala Phe Thr
         115                 120                 125

Lys Asn Gly Ser Gly Ala Val Phe Pro Val Ala Gly Ala Asp Val Gln
 130                 135                 140

Thr Leu Arg Glu Arg Leu Ile Asp Ala Leu Glu Ser His His Asp Thr
145                 150                 155                 160

Trp Pro Pro Ala Cys Pro Pro Leu Glu Pro Ala Lys Leu Glu Glu Ile
                165                 170                 175

Asp Gly Phe Phe Ala Arg Asn Asn Glu Glu Tyr Leu Ala Leu Ile Phe
                180                 185                 190

Glu Lys Gly Gly Ser Tyr Leu Gly Arg Glu Val Ala Leu Asp Leu Ser
         195                 200                 205

Gln His Lys Gly Val Ala Val Arg Arg Val Leu Asn Thr Glu Ala Asn
 210                 215                 220

Val Val Arg Lys Phe Gly Val Thr Asp Phe Pro Ser Cys Tyr Leu Leu
225                 230                 235                 240

Phe Arg Asn Gly Ser Val Ser Arg Val Pro Val Leu Met Glu Ser Arg
                245                 250                 255

Ser Phe Tyr Thr Ala Tyr Leu Gln Arg Leu Ser Gly Leu Thr Arg Glu
                260                 265                 270

Ala Ala Gln Thr Thr Val Ala Pro Thr Thr Ala Asn Lys Ile Ala Pro
         275                 280                 285

Thr Val Trp Lys Leu Ala Asp Arg Ser Lys Ile Tyr Met Ala Asp Leu
290                 295                 300

Glu Ser Ala Leu His Tyr Ile Leu Arg Ile Glu Val Gly Arg Phe Pro
305                 310                 315                 320

Val Leu Glu Gly Gln Arg Leu Val Ala Leu Lys Lys Phe Val Ala Val
                325                 330                 335

Leu Ala Lys Tyr Phe Pro Gly Arg Pro Leu Val Gln Asn Phe Leu His
            340                 345                 350

Ser Val Asn Glu Trp Leu Lys Arg Gln Lys Arg Asn Lys Ile Pro Tyr
            355                 360                 365

Ser Phe Phe Lys Thr Ala Leu Asp Asp Arg Lys Glu Gly Ala Val Leu
            370                 375                 380

Ala Lys Lys Val Asn Trp Ile Gly Cys Gln Gly Ser Glu Pro His Phe
385                 390                 395                 400

Arg Gly Phe Pro Cys Ser Leu Trp Val Leu Phe His Phe Leu Thr Val
                405                 410                 415

Gln Ala Ala Arg Gln Asn Val Asp His Ser Gln Glu Ala Ala Lys Ala
            420                 425                 430

Lys Glu Val Leu Pro Ala Ile Arg Gly Tyr Val His Tyr Phe Phe Gly
            435                 440                 445
```

```
Cys Arg Asp Cys Ala Ser His Phe Glu Gln Met Ala Ala Ser Met
            450                 455                 460
His Arg Val Gly Ser Pro Asn Ala Ala Val Leu Trp Leu Trp Ser Ser
465                 470                 475                 480
His Asn Arg Val Asn Ala Arg Leu Ala Gly Ala Pro Ser Glu Asp Pro
                    485                 490                 495
Gln Phe Pro Lys Val Gln Trp Pro Pro Arg Glu Leu Cys Ser Ala Cys
            500                 505                 510
His Asn Glu Arg Leu Asp Val Pro Val Trp Asp Val Glu Ala Thr Leu
            515                 520                 525
Asn Phe Leu Lys Ala His Phe Ser Pro Ser Asn Ile Ile Leu Asp Phe
530                 535                 540
Pro Ala Ala Gly Ser Ala Ala Arg Arg Asp Val Gln Asn Val Ala Ala
545                 550                 555                 560
Ala Pro Glu Leu Ala Met Gly Ala Leu Glu Leu Glu Ser Arg Asn Ser
                565                 570                 575
Thr Leu Asp Pro Gly Lys Pro Glu Met Met Lys Ser Pro Thr Asn Thr
            580                 585                 590
Thr Pro His Val Pro Ala Glu Gly Pro Glu Leu Ile
            595                 600
```

(2) INFORMATION FOR SEQ ID NO:5:

(i) SEQUENCE CHARACTERISTICS:
        (A) LENGTH: 2103 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
ATGAGGAGGT GCAACAGCGG CTCCGGGCCG CCGCCGTCGC TGCTGCTGCT GCTGCTGTGG     60
CTGCTCGCGG TTCCCGGCGC TAACGCGGCC CCGCGGTCGG CGCTCTATTC GCCTTCCGAC    120
CCGCTGACGC TGCTGCAGGC GGACACGGTG CGCGGCGCGG TGCTGGGCTC CCGCAGCGCC    180
TGGGCCGTGG AGTTCTTCGC CTCCTGGTGC GGCCACTGCA TCGCCTTCGC CCCGACGTGG    240
AAGGCGCTGG CCGAAGACGT CAAAGCCTGG AGGCCGGCCC TGTATCTCGC CGCCCTGGAC    300
TGTGCTGAGG AGACCAACAG TGCAGTCTGC AGAGACTTCA ACATCCCTGG CTTCCCGACT    360
GTGAGGTTCT TCAAGGCCTT TACCAAGAAC GGCTCGGGAG CAGTATTTCC AGTGGCTGGT    420
GCTGACGTGC AGACGCTGCG GGAGAGGCTC ATTGACGCCC TGGAGTCCCA TCATGACACG    480
TGGCCCCCAG CCTGTCCCCC ACTGGAGCCT GCCAAGCTGG AGGAGATTGA TGGATTCTTT    540
GCGAGAAATA ACGAAGAGTA CCTGGCTCTG ATCTTTGAAA AGGGAGGCTC CTACCTGGGT    600
AGAGAGGTGG CTCTGGACCT GTCCCAGCAC AAAGGCGTGG CGGTGCGCAG GGTGCTGAAC    660
ACAGAGGCCA ATGTGGTGAG AAAGTTTGGT GTCACCGACT TCCCCTCTTG CTACCTGCTG    720
TTCCGGAATG GCTCTGTCTC CCGAGTCCCC GTGCTCATGG AATCCAGGTC CTTCTATACC    780
GCTTACCTGC AGAGACTCTC TGGGCTCACC AGGGAGGCTG CCCAGACCAC AGTTGCACCA    840
ACCACTGCTA ACAAGATAGC TCCCACTGTT TGGAAATTGG CAGATCGCTC CAAGATCTAC    900
ATGGCTGACC TGGAATCTGC ACTGCACTAC ATCCTGCGGA TAGAAGTGGG CAGGTTCCCG    960
GTCCTGGAAG GCAGCGCCT GGTGGCCCTG AAAAAGTTTG TGGCAGTGCT GGCCAAGTAT   1020
TTCCCTGGCC GGCCCTTAGT CCAGAACTTC CTGCACTCCG TGAATGAATG GCTCAAGAGG   1080
```

-continued

```
CAGAAGAGAA ATAAAATTCC CTACAGTTTC TTTAAAACTG CCCTGGACGA CAGGAAAGAG   1140

GGTGCCGTTC TTGCCAAGAA GGTGAACTGG ATTGGCTGCC AGGGGAGTGA GCCGCATTTC   1200

CGGGGCTTTC CCTGCTCCCT GTGGGTCCTC TTCCACTTCT TGACTGTGCA GGCAGCTCGC   1260

CAAAATGTAG ACCACTCACA GGAAGCAGCC AAGGCCAAGG AGGTCCTCCC AGCCATCCGA   1320

GGCTACGTGC ACTACTTCTT CGGCTGCCGA GACTGCGCTA GCCACTTCGA GCAGATGGCT   1380

GCTGCCTCCA TGCACCGGGT GGGGAGTCCC AACGCCGCTG TCCTCTGGCT CTGGTCTAGC   1440

CACAACAGGG TCAATGCTCG CCTTGCAGGT GCCCCCAGCG AGGACCCCCA GTTCCCCAAG   1500

GTGCAGTGGC CACCCCGTGA ACTTTGTTCT GCCTGCCACA ATGAACGCCT GGATGTGCCC   1560

GTGTGGGACG TGGAAGCCAC CCTCAACTTC CTCAAGGCCC ACTTCTCCCC AAGCAACATC   1620

ATCCTGGACT TCCCTGCAGC TGGGTCAGCT GCCCGGAGGG ATGTGCAGAA TGTGGCAGCC   1680

GCCCCAGAGC TGGCGATGGG AGCCCTGGAG CTGGAAAGCC GGAATTCAAC TCTGGACCCT   1740

GGGAAGCCTG AGATGATGAA GTCCCCCACA ACACCACCC CACATGTGCC GGCTGAGGGA    1800

CCTGAGGCAA GTCGACCCCC GAAGCTGCAC CCTGGCCTCA GAGCTGCACC AGGCCAGGAG   1860

CCTCCTGAGC ACATGGCAGA GCTTCAGAGG AATGAGCAGG AGCAGCCGCT TGGGCAGTGG   1920

CACTTGAGCA AGCGAGACAC AGGGGCTGCA TTGCTGGCTG AGTCCAGGGC TGAGAAGAAC   1980

CGCCTCTGGG GCCCTTTGGA GGTCAGGCGC GTGGGCCGCA GCTCCAAGCA GCTGGTCGAC   2040

ATCCCTGAGG GCCAGCTGGA GGCCCGAGCT GGACGGGGCC GAGGCCAGTG GCTGCAGCTT   2100

ATT                                                                 2103
```

(2) INFORMATION FOR SEQ ID NO:6:

(i) SEQUENCE CHARACTERISTICS:
        (A) LENGTH: 701 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Arg Arg Cys Asn Ser Gly Ser Gly Pro Pro Ser Leu Leu Leu
1               5                  10                  15

Leu Leu Leu Trp Leu Leu Ala Val Pro Gly Ala Asn Ala Ala Pro Arg
            20                  25                  30

Ser Ala Leu Tyr Ser Pro Ser Asp Pro Leu Thr Leu Leu Gln Ala Asp
                35                  40                  45

Thr Val Arg Gly Ala Val Leu Gly Ser Arg Ser Ala Trp Ala Val Glu
        50                  55                  60

Phe Phe Ala Ser Trp Cys Gly His Cys Ile Ala Phe Ala Pro Thr Trp
65                  70                  75                  80

Lys Ala Leu Ala Glu Asp Val Lys Ala Trp Arg Pro Ala Leu Tyr Leu
                85                  90                  95

Ala Ala Leu Asp Cys Ala Glu Glu Thr Asn Ser Ala Val Cys Arg Asp
                100                 105                 110

Phe Asn Ile Pro Gly Phe Pro Thr Val Arg Phe Phe Lys Ala Phe Thr
            115                 120                 125

Lys Asn Gly Ser Gly Ala Val Phe Pro Val Ala Gly Ala Asp Val Gln
        130                 135                 140

Thr Leu Arg Glu Arg Leu Ile Asp Ala Leu Glu Ser His His Asp Thr
145                 150                 155                 160
```

```
Trp Pro Pro Ala Cys Pro Pro Leu Glu Pro Ala Lys Leu Glu Glu Ile
                165                 170                 175

Asp Gly Phe Phe Ala Arg Asn Asn Glu Glu Tyr Leu Ala Leu Ile Phe
            180                 185                 190

Glu Lys Gly Gly Ser Tyr Leu Gly Arg Glu Val Ala Leu Asp Leu Ser
        195                 200                 205

Gln His Lys Gly Val Ala Val Arg Arg Val Leu Asn Thr Glu Ala Asn
    210                 215                 220

Val Val Arg Lys Phe Gly Val Thr Asp Phe Pro Ser Cys Tyr Leu Leu
225                 230                 235                 240

Phe Arg Asn Gly Ser Val Ser Arg Val Pro Val Leu Met Glu Ser Arg
                245                 250                 255

Ser Phe Tyr Thr Ala Tyr Leu Gln Arg Leu Ser Gly Leu Thr Arg Glu
            260                 265                 270

Ala Ala Gln Thr Thr Val Ala Pro Thr Thr Ala Asn Lys Ile Ala Pro
        275                 280                 285

Thr Val Trp Lys Leu Ala Asp Arg Ser Lys Ile Tyr Met Ala Asp Leu
    290                 295                 300

Glu Ser Ala Leu His Tyr Ile Leu Arg Ile Glu Val Gly Arg Phe Pro
305                 310                 315                 320

Val Leu Glu Gly Gln Arg Leu Val Ala Leu Lys Lys Phe Val Ala Val
                325                 330                 335

Leu Ala Lys Tyr Phe Pro Gly Arg Pro Leu Val Gln Asn Phe Leu His
            340                 345                 350

Ser Val Asn Glu Trp Leu Lys Arg Gln Lys Arg Asn Lys Ile Pro Tyr
        355                 360                 365

Ser Phe Phe Lys Thr Ala Leu Asp Asp Arg Lys Glu Gly Ala Val Leu
    370                 375                 380

Ala Lys Lys Val Asn Trp Ile Gly Cys Gln Gly Ser Glu Pro His Phe
385                 390                 395                 400

Arg Gly Phe Pro Cys Ser Leu Trp Val Leu Phe His Phe Leu Thr Val
                405                 410                 415

Gln Ala Ala Arg Gln Asn Val Asp His Ser Gln Glu Ala Ala Lys Ala
            420                 425                 430

Lys Glu Val Leu Pro Ala Ile Arg Gly Tyr Val His Tyr Phe Phe Gly
        435                 440                 445

Cys Arg Asp Cys Ala Ser His Phe Glu Gln Met Ala Ala Ala Ser Met
    450                 455                 460

His Arg Val Gly Ser Pro Asn Ala Ala Val Leu Trp Leu Trp Ser Ser
465                 470                 475                 480

His Asn Arg Val Asn Ala Arg Leu Ala Gly Ala Pro Ser Glu Asp Pro
                485                 490                 495

Gln Phe Pro Lys Val Gln Trp Pro Pro Arg Glu Leu Cys Ser Ala Cys
            500                 505                 510

His Asn Glu Arg Leu Asp Val Pro Val Trp Asp Val Glu Ala Thr Leu
        515                 520                 525

Asn Phe Leu Lys Ala His Phe Ser Pro Ser Asn Ile Ile Leu Asp Phe
    530                 535                 540

Pro Ala Ala Gly Ser Ala Ala Arg Arg Asp Val Gln Asn Val Ala Ala
545                 550                 555                 560

Ala Pro Glu Leu Ala Met Gly Ala Leu Glu Leu Glu Ser Arg Asn Ser
                565                 570                 575

Thr Leu Asp Pro Gly Lys Pro Glu Met Met Lys Ser Pro Thr Asn Thr
```

-continued

```
                580                 585                 590
Thr Pro His Val Pro Ala Glu Gly Pro Glu Ala Ser Arg Pro Pro Lys
            595                 600                 605
Leu His Pro Gly Leu Arg Ala Pro Gly Gln Glu Pro Pro Glu His
        610                 615                 620
Met Ala Glu Leu Gln Arg Asn Glu Gln Gln Pro Leu Gly Gln Trp
625                 630                 635                 640
His Leu Ser Lys Arg Asp Thr Gly Ala Ala Leu Leu Ala Glu Ser Arg
                645                 650                 655
Ala Glu Lys Asn Arg Leu Trp Gly Pro Leu Glu Val Arg Arg Val Gly
            660                 665                 670
Arg Ser Ser Lys Gln Leu Val Asp Ile Pro Glu Gly Gln Leu Glu Ala
        675                 680                 685
Arg Ala Gly Arg Gly Arg Gly Gln Trp Leu Gln Leu Ile
        690                 695                 700
```

(2) INFORMATION FOR SEQ ID NO:7:

(i) SEQUENCE CHARACTERISTICS:
        (A) LENGTH: 2103 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
ATGAGGAGGT GCAACAGCGG CTCCGGGCCG CCGCCGTCGC TGCTGCTGCT GCTGCTGTGG      60
CTGCTCGCGG TTCCCGGCGC TAACGCGGCC CCGCGGTCGG CGCTCTATTC GCCTTCCGAC     120
CCGCTGACGC TGCTGCAGGC GGACACGGTG CGCGGCGCGG TGCTGGGCTC CGCAGCGCC      180
TGGGCCGTGG AGTTCTTCGC CTCCTGGTGC GGCCACTGCA TCGCCTTCGC CCCGACGTGG     240
AAGGCGCTGG CCGAAGACGT CAAAGCCTGG AGGCCGGCCC TGTATCTCGC CGCCCTGGAC     300
TGTGCTGAGG AGACCAACAG TGCAGTCTGC AGAGACTTCA ACATCCCTGG CTTCCCGACT     360
GTGAGGTTCT TCAAGGCCTT TACCAAGAAC GGCTCGGGAG CAGTATTTCC AGTGGCTGGT     420
GCTGACGTGC AGACGCTGCG GGAGAGGCTC ATTGACGCCC TGGAGTCCCA TCATGACACG     480
TGGCCCCCAG CCTGTCCCCC ACTGGAGCCT GCCAAGCTGG AGGAGATTGA TGGATTCTTT     540
GCGAGAAATA ACGAAGAGTA CCTGGCTCTG ATCTTTGAAA AGGGAGGCTC CTACCTGGGT     600
AGAGAGGTGG CTCTGGACCT GTCCCAGCAC AAAGGCGTGG CGGTGCGCAG GGTGCTGAAC     660
ACAGAGGCCA ATGTGGTGAG AAAGTTTGGT GTCACCGACT TCCCCTCTTG CTACCTGCTG     720
TTCCGGAATG GCTCTGTCTC CCGAGTCCCC GTGCTCATGG AATCCAGGTC CTTCTATACC     780
GCTTACCTGC AGAGACTCTC TGGGCTCACC AGGGAGGCTG CCCAGACCAC AGTTGCACCA     840
ACCACTGCTA ACAAGATAGC TCCCACTGTT TGGAAATTGG CAGATCGCTC CAAGATCTAC     900
ATGGCTGACC TGGAATCTGC ACTGCACTAC ATCCTGCGGA TAGAAGTGGG CAGGTTCCCG     960
GTCCTGGAAG GCAGCGCCT GGTGGCCCTG AAAAAGTTTG TGGCAGTGCT GGCCAAGTAT    1020
TTCCCTGGCC GGCCCTTAGT CCAGAACTTC CTGCACTCCG TGAATGAATG GCTCAAGAGG    1080
CAGAAGAGAA ATAAAATTCC CTACAGTTTC TTTAAAACTG CCCTGGACGA CAGGAAAGAG    1140
GGTGCCGTTC TTGCCAAGAA GGTGAACTGG ATTGGCTGCC AGGGGAGTGA GCCGCATTTC    1200
GGGGGCTTTC CCTGCTCCCT GTGGGTCCTC TTCCACTTCT TGACTGTGCA GGCAGCTCGG    1260
CAAAATGTAG ACCACTCACA GGAAGCAGCC AAGGCCAAGG AGGTCCTCCC AGCCATCCGA    1320
```

```
GGCTACGTGC ACTACTTCTT CGGCTGCCGA GACTGCGCTA GCCACTTCGA GCAGATGGCT      1380

GCTGCCTCCA TGCACCGGGT GGGGAGTCCC AACGCCGCTG TCCTCTGGCT CTGGTCTAGC      1440

CACAACAGGG TCAATGCTCG CCTTGCAGGT GCCCCCAGCG AGGACCCCCA GTTCCCCAAG      1500

GTGCAGTGGC CACCCCGTGA ACTTTGTTCT GCCTGCCACA ATGAACGCCT GGATGTGCCC      1560

GTGTGGGACG TGGAAGCCAC CCTCAACTTC CTCAAGGCCC ACTTCTCCCC AAGCAACATC      1620

ATCCTGGACT TCCCTGCAGC TGGGTCAGCT GCCCGGAGGG ATGTGCAGAA TGTGGCAGCC      1680

GCCCCAGAGC TGGCGATGGG AGCCCTGGAG CTGGAAAGCC GGAATTCAAC TCTGGACCCT      1740

GGGAAGCCTG AGATGATGAA GTCCCCCACA AACACCACCC CACATGTGCC GGCTGAGGGA      1800

CCTGAGGCAA GTCGACCCCC GAAGCTGCAC CCTGGCCTCA GAGCTGCACC AGGCCAGGAG      1860

CCTCCTGAGC ACATGGCAGA GCTTCAGAGG AATGAGCAGG AGCAGCCGCT TGGGCAGTGG      1920

CACTTGAGCA AGCGAGACAC AGGGGCTGCA TTGCTGGCTG AGTCCAGGGC TGAGAAGAAC      1980

CGCCTCTGGG GCCCTTTGGA GGTCAGGCGC GTGGGCCGCA GCTCCAAGCA GCTGGTCGAC      2040

ATCCCTGAGG GCCAGCTGGA GGCCCGAGCT GGACGGGGCC GAGGCCAGTG GCTGCAGCTT      2100

ATT                                                                   2103

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

TGGAGTTCTT CGCCTCCTGG T                                                21

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

TGGTGAGCCC AGAGAGTCTC TG                                               22

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

ATGATGGGAC TCCACGGCGT CAAT                                             24

(2) INFORMATION FOR SEQ ID NO:11:

(i) SEQUENCE CHARACTERISTICS:
        (A) LENGTH: 24 base pairs
```

```
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:11:

GGGAAGCCAG GGATGTTGAA GTCT                                              24

(2) INFORMATION FOR SEQ ID NO:12:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:12:

CGAAGAGTAC CTGGCTCTGA TC                                                22
```